(12) United States Patent
Marczyk et al.

(10) Patent No.: US 11,457,942 B2
(45) Date of Patent: *Oct. 4, 2022

(54) SURGICAL DEVICE WITH ARTICULATION AND WRIST ROTATION

(71) Applicant: Covidien LP, Mansfield, MA (US)

(72) Inventors: Stanislaw Marczyk, Stratford, CT (US); Russell Pribanic, Roxbury, CT (US); Kenneth W. Horton, Jr., South Glastonbury, CT (US)

(73) Assignee: Covidien LP, Mansfield, MA (US)

( * ) Notice: Subject to any disclaimer, the term of this patent is extended or adjusted under 35 U.S.C. 154(b) by 462 days.

This patent is subject to a terminal disclaimer.

(21) Appl. No.: 16/571,066

(22) Filed: Sep. 14, 2019

(65) Prior Publication Data

US 2020/0008830 A1 Jan. 9, 2020

Related U.S. Application Data

(60) Division of application No. 15/422,636, filed on Feb. 2, 2017, now Pat. No. 10,448,964, which is a
(Continued)

(51) Int. Cl.
*A61B 17/29* (2006.01)
*A61B 17/00* (2006.01)

(52) U.S. Cl.
CPC .......... *A61B 17/2909* (2013.01); *A61B 17/29* (2013.01); *A61B 2017/00327* (2013.01);
(Continued)

(58) Field of Classification Search
None
See application file for complete search history.

(56) References Cited

U.S. PATENT DOCUMENTS

| 2,453,862 | A | * | 11/1948 | Salisbury | ........... | A61B 1/00177 |
| | | | | | | 600/146 |
| 3,079,606 | A | | 3/1963 | Bobrov et al. | | |

(Continued)

FOREIGN PATENT DOCUMENTS

| AU | 5476586 A | 9/1986 |
| AU | 198654765 | 9/1986 |

(Continued)

*Primary Examiner* — Carl H Layno
*Assistant Examiner* — Manolis Pahakis
(74) *Attorney, Agent, or Firm* — Carter, Deluca & Farrell LLP

(57) ABSTRACT

A surgical instrument comprising a handle assembly, an elongated shaft, an end effector, a rotation mechanism, and an articulation mechanism is disclosed. The rotation mechanism is disposed in mechanical cooperation with the handle assembly and effects rotation of the end effector about the second longitudinal axis. The articulation mechanism is disposed in mechanical cooperation with the handle assembly and effects movement of the end effector from a first position where the first longitudinal axis is substantially aligned with the second longitudinal axis to a second position where the second longitudinal axis is displaced from the first longitudinal axis. The articulation mechanism comprises a first articulation control disposed in mechanical cooperation with the handle assembly, a first cable and a second cable. Actuation of the first articulation control in a first direction causes the first cable to move distally and causes the second cable to move proximally.

17 Claims, 20 Drawing Sheets

Related U.S. Application Data continuation of application No. 13/543,931, filed on Jul. 9, 2012, now abandoned.

(60) Provisional application No. 61/505,604, filed on Jul. 8, 2011.

(52) U.S. Cl.
CPC . *A61B 2017/291* (2013.01); *A61B 2017/2927* (2013.01); *A61B 2017/2929* (2013.01)

(56) References Cited

U.S. PATENT DOCUMENTS

| | | |
|---|---|---|
| 3,190,286 A | 6/1965 | Stokes |
| 3,252,524 A | 5/1966 | Van Der Lely et al. |
| 3,490,675 A | 1/1970 | Green et al. |
| 3,499,591 A | 3/1970 | Green |
| 3,557,780 A * | 1/1971 | Sato .................. A61B 1/0055 600/141 |
| 3,572,325 A * | 3/1971 | Bazell et al. ...... A61B 1/00165 600/164 |
| 3,605,725 A | 9/1971 | Bentov |
| 3,610,231 A | 10/1971 | Takahashi et al. |
| 3,777,538 A | 12/1973 | Weatherly et al. |
| 3,788,303 A | 1/1974 | Hall |
| 3,882,854 A | 5/1975 | Hulka et al. |
| 4,027,510 A | 6/1977 | Hiltebrandt |
| 4,086,926 A | 5/1978 | Green et al. |
| 4,207,873 A | 6/1980 | Kruy |
| 4,244,372 A | 1/1981 | Kapitanov et al. |
| 4,429,695 A | 2/1984 | Green |
| 4,483,326 A | 11/1984 | Yamaka et al. |
| 4,499,895 A | 2/1985 | Takayama |
| 4,505,414 A | 3/1985 | Filipi |
| 4,520,817 A | 6/1985 | Green |
| 4,530,568 A | 7/1985 | Haduch et al. |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,762,118 A | 8/1988 | Lia et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,911,148 A * | 3/1990 | Sosnowski ......... A61B 1/00165 600/164 |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A * | 5/1994 | Green .............. A61B 17/07207 227/19 |
| 5,318,221 A | 6/1994 | Green et al. |
| 5,325,845 A * | 7/1994 | Adair .................. A61B 1/0055 604/95.04 |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A * | 10/1994 | Green ................ A61B 17/0684 606/139 |
| 5,358,478 A * | 10/1994 | Thompson ........ A61M 25/0144 604/95.04 |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,388,568 A * | 2/1995 | van der Heide .. A61M 25/0136 600/146 |
| 5,389,098 A | 2/1995 | Tsuruta et al. |
| 5,395,033 A | 3/1995 | Byrne et al. |
| 5,395,034 A | 3/1995 | Mien et al. |
| 5,397,046 A | 3/1995 | Savage et al. |
| 5,397,324 A | 3/1995 | Carroll et al. |
| 5,402,793 A | 4/1995 | Gruner et al. |
| 5,403,312 A | 4/1995 | Yates et al. |
| 5,405,072 A | 4/1995 | Zlock et al. |
| 5,405,344 A * | 4/1995 | Williamson ....... A61B 17/1285 606/1 |
| 5,407,293 A | 4/1995 | Crainich |
| 5,409,498 A * | 4/1995 | Braddock .......... A61B 17/1285 606/139 |
| 5,413,107 A * | 5/1995 | Oakley ............. A61M 25/0136 600/463 |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,454,827 A | 10/1995 | Aust et al. |
| 5,456,401 A | 10/1995 | Green et al. |
| 5,462,527 A | 10/1995 | Stevens-Wright et al. |
| 5,464,300 A | 11/1995 | Crainich |
| 5,465,895 A | 11/1995 | Knodel et al. |

(56) References Cited

U.S. PATENT DOCUMENTS

| | | | |
|---|---|---|---|
| 5,467,911 A | 11/1995 | Tsuruta et al. | |
| 5,470,007 A | 11/1995 | Plyley et al. | |
| 5,470,010 A | 11/1995 | Rothfuss et al. | |
| 5,472,132 A | 12/1995 | Savage et al. | |
| 5,474,566 A | 12/1995 | Alesi et al. | |
| 5,476,206 A | 12/1995 | Green et al. | |
| 5,478,003 A * | 12/1995 | Green | A61B 17/07207 227/176.1 |
| 5,480,089 A | 1/1996 | Blewett | |
| 5,482,197 A | 1/1996 | Green et al. | |
| 5,484,095 A | 1/1996 | Green et al. | |
| 5,484,451 A | 1/1996 | Akopov et al. | |
| 5,485,947 A | 1/1996 | Olson et al. | |
| 5,485,952 A | 1/1996 | Fontayne | |
| 5,486,185 A | 1/1996 | Freitas et al. | |
| 5,487,499 A | 1/1996 | Sorrentino et al. | |
| 5,487,500 A | 1/1996 | Knodel et al. | |
| 5,489,058 A | 2/1996 | Plyley et al. | |
| 5,490,856 A | 2/1996 | Person et al. | |
| 5,497,933 A | 3/1996 | DeFonzo et al. | |
| 5,501,689 A | 3/1996 | Green et al. | |
| 5,505,363 A | 4/1996 | Green et al. | |
| 5,507,426 A | 4/1996 | Young et al. | |
| 5,518,163 A | 5/1996 | Hooven | |
| 5,518,164 A | 5/1996 | Hooven | |
| 5,529,235 A | 6/1996 | Boiarski et al. | |
| 5,531,744 A | 7/1996 | Nardella et al. | |
| 5,535,934 A | 7/1996 | Boiarski et al. | |
| 5,535,935 A | 7/1996 | Vidal et al. | |
| 5,535,937 A | 7/1996 | Boiarski et al. | |
| 5,540,375 A * | 7/1996 | Bolanos | A61B 17/072 227/19 |
| 5,542,594 A | 8/1996 | McKean et al. | |
| 5,549,628 A | 8/1996 | Cooper et al. | |
| 5,551,622 A | 9/1996 | Yoon | |
| 5,553,765 A | 9/1996 | Knodel et al. | |
| 5,554,164 A | 9/1996 | Wilson et al. | |
| 5,554,169 A | 9/1996 | Green et al. | |
| 5,560,530 A | 10/1996 | Bolanos et al. | |
| 5,560,532 A * | 10/1996 | DeFonzo | A61B 17/0684 227/176.1 |
| 5,562,239 A | 10/1996 | Boiarski et al. | |
| 5,562,241 A | 10/1996 | Knodel et al. | |
| 5,562,682 A | 10/1996 | Oberlin et al. | |
| 5,562,701 A | 10/1996 | Huitema et al. | |
| 5,564,615 A * | 10/1996 | Bishop | A61B 17/0682 227/19 |
| 5,571,116 A | 11/1996 | Bolanos et al. | |
| 5,573,169 A | 11/1996 | Green et al. | |
| 5,573,543 A | 11/1996 | Akopov et al. | |
| 5,575,799 A | 11/1996 | Bolanos et al. | |
| 5,575,803 A | 11/1996 | Cooper et al. | |
| 5,577,654 A | 11/1996 | Bishop | |
| 5,579,107 A | 11/1996 | Wright et al. | |
| 5,584,425 A | 12/1996 | Savage et al. | |
| 5,586,711 A | 12/1996 | Plyley et al. | |
| 5,588,580 A | 12/1996 | Paul et al. | |
| 5,588,581 A | 12/1996 | Conlon et al. | |
| 5,597,107 A | 1/1997 | Knodel et al. | |
| 5,601,224 A | 2/1997 | Bishop et al. | |
| 5,607,095 A | 3/1997 | Smith et al. | |
| 5,615,820 A | 4/1997 | Viola | |
| 5,618,291 A | 4/1997 | Thompson et al. | |
| 5,624,452 A | 4/1997 | Yates | |
| 5,626,587 A | 5/1997 | Bishop et al. | |
| 5,628,446 A | 5/1997 | Geiste et al. | |
| 5,630,539 A | 5/1997 | Plyley et al. | |
| 5,630,540 A | 5/1997 | Blewett | |
| 5,630,541 A | 5/1997 | Williamson, IV et al. | |
| 5,632,432 A | 5/1997 | Schulze et al. | |
| 5,634,584 A | 6/1997 | Okorocha et al. | |
| 5,636,780 A | 6/1997 | Green et al. | |
| 5,645,209 A | 7/1997 | Green et al. | |
| 5,647,526 A | 7/1997 | Green et al. | |
| 5,651,491 A | 7/1997 | Heaton et al. | |
| 5,653,373 A | 8/1997 | Green et al. | |
| 5,653,374 A | 8/1997 | Young et al. | |
| 5,653,721 A | 8/1997 | Knodel et al. | |
| 5,655,698 A | 8/1997 | Yoon | |
| 5,657,921 A | 8/1997 | Young et al. | |
| 5,658,300 A | 8/1997 | Bito et al. | |
| 5,662,258 A | 9/1997 | Knodel et al. | |
| 5,662,259 A | 9/1997 | Yoon | |
| 5,662,260 A | 9/1997 | Yoon | |
| 5,662,662 A * | 9/1997 | Bishop | A61B 17/0684 606/139 |
| 5,662,666 A | 9/1997 | Onuki et al. | |
| 5,665,085 A | 9/1997 | Nardella | |
| 5,667,517 A | 9/1997 | Hooven | |
| 5,669,544 A | 9/1997 | Schulze et al. | |
| 5,673,840 A | 10/1997 | Schulze et al. | |
| 5,673,841 A | 10/1997 | Schulze et al. | |
| 5,673,842 A | 10/1997 | Bittner et al. | |
| 5,676,674 A | 10/1997 | Bolanos et al. | |
| 5,680,981 A | 10/1997 | Mililli et al. | |
| 5,680,982 A | 10/1997 | Schulze et al. | |
| 5,680,983 A | 10/1997 | Plyley et al. | |
| 5,690,269 A | 11/1997 | Bolanos et al. | |
| 5,690,675 A | 11/1997 | Sawyer et al. | |
| 5,692,668 A | 12/1997 | Schulze et al. | |
| 5,697,542 A | 12/1997 | Knodel et al. | |
| 5,702,408 A | 12/1997 | Wales et al. | |
| 5,702,409 A | 12/1997 | Rayburn et al. | |
| 5,704,534 A | 1/1998 | Huitema et al. | |
| 5,706,997 A | 1/1998 | Green et al. | |
| 5,709,334 A | 1/1998 | Sorrentino et al. | |
| 5,711,472 A | 1/1998 | Bryan | |
| 5,713,505 A | 2/1998 | Huitema | |
| 5,715,988 A | 2/1998 | Palmer | |
| 5,716,366 A | 2/1998 | Yates | |
| 5,718,359 A | 2/1998 | Palmer et al. | |
| 5,725,536 A | 3/1998 | Oberlin et al. | |
| 5,725,554 A | 3/1998 | Simon et al. | |
| 5,728,110 A | 3/1998 | Vidal et al. | |
| 5,732,806 A | 3/1998 | Foshee et al. | |
| 5,735,848 A | 4/1998 | Yates et al. | |
| 5,743,456 A * | 4/1998 | Jones | A61B 17/0684 227/176.1 |
| 5,749,893 A | 5/1998 | Vidal et al. | |
| 5,752,644 A | 5/1998 | Bolanos et al. | |
| 5,762,255 A | 6/1998 | Chrisman et al. | |
| 5,762,256 A | 6/1998 | Mastri et al. | |
| 5,766,196 A * | 6/1998 | Griffiths | A61B 17/29 606/174 |
| 5,769,303 A | 6/1998 | Knodel et al. | |
| 5,769,892 A | 6/1998 | Kingwell | |
| 5,772,099 A | 6/1998 | Gravener | |
| 5,772,673 A | 6/1998 | Cuny et al. | |
| 5,779,130 A | 7/1998 | Alesi et al. | |
| 5,779,131 A | 7/1998 | Knodel et al. | |
| 5,779,132 A | 7/1998 | Knodel et al. | |
| 5,782,396 A | 7/1998 | Mastri et al. | |
| 5,782,397 A | 7/1998 | Koukline | |
| 5,782,834 A | 7/1998 | Lucey et al. | |
| 5,785,232 A | 7/1998 | Vidal et al. | |
| 5,797,536 A | 8/1998 | Smith et al. | |
| 5,797,537 A | 8/1998 | Oberlin et al. | |
| 5,797,538 A | 8/1998 | Heaton et al. | |
| 5,810,811 A | 9/1998 | Yates et al. | |
| 5,810,855 A | 9/1998 | Rayburn et al. | |
| 5,814,055 A | 9/1998 | Knodel et al. | |
| 5,814,057 A | 9/1998 | Oi et al. | |
| 5,816,471 A | 10/1998 | Plyley et al. | |
| 5,817,109 A | 10/1998 | McGarry et al. | |
| 5,820,009 A | 10/1998 | Melling et al. | |
| 5,823,066 A | 10/1998 | Huitema et al. | |
| 5,826,776 A | 10/1998 | Schulze et al. | |
| 5,829,662 A | 11/1998 | Allen et al. | |
| 5,833,695 A | 11/1998 | Yoon | |
| 5,836,147 A | 11/1998 | Schnipke | |
| 5,862,972 A | 1/1999 | Green et al. | |
| 5,865,361 A | 2/1999 | Milliman et al. | |
| 5,871,135 A | 2/1999 | Williamson IV et al. | |
| 5,873,873 A | 2/1999 | Smith et al. | |

(56) References Cited

U.S. PATENT DOCUMENTS

| | | | |
|---|---|---|---|
| 5,878,938 A | 3/1999 | Bittner et al. | |
| 5,891,088 A * | 4/1999 | Thompson | A61M 25/0136 |
| | | | 604/524 |
| 5,893,506 A | 4/1999 | Powell | |
| 5,894,979 A | 4/1999 | Powell | |
| 5,897,562 A | 4/1999 | Bolanos et al. | |
| 5,901,895 A * | 5/1999 | Heaton | A61B 17/07207 |
| | | | 227/176.1 |
| 5,911,352 A | 6/1999 | Racenet et al. | |
| 5,911,353 A | 6/1999 | Bolanos et al. | |
| 5,918,791 A | 7/1999 | Sorrentino et al. | |
| 5,919,198 A | 7/1999 | Graves, Jr. et al. | |
| 5,922,001 A | 7/1999 | Yoon | |
| 5,931,847 A | 8/1999 | Bittner et al. | |
| 5,941,442 A | 8/1999 | Geiste et al. | |
| 5,954,259 A | 9/1999 | Viola et al. | |
| 5,954,654 A * | 9/1999 | Eaton | A61M 25/0136 |
| | | | 600/459 |
| 5,964,774 A | 10/1999 | McKean et al. | |
| 5,980,510 A | 11/1999 | Tsonton et al. | |
| 5,988,479 A | 11/1999 | Palmer | |
| 6,004,335 A | 12/1999 | Vaitekunas et al. | |
| 6,010,054 A | 1/2000 | Johnson et al. | |
| 6,032,849 A | 3/2000 | Mastri et al. | |
| 6,045,560 A | 4/2000 | McKean et al. | |
| 6,063,097 A | 5/2000 | Oi et al. | |
| 6,079,606 A | 6/2000 | Milliman et al. | |
| 6,099,551 A | 8/2000 | Gabbay | |
| 6,109,500 A | 8/2000 | Alli et al. | |
| 6,131,789 A | 10/2000 | Schulze et al. | |
| 6,131,790 A | 10/2000 | Piraka | |
| 6,155,473 A | 12/2000 | Tompkins et al. | |
| 6,162,208 A * | 12/2000 | Hipps | A61F 2/2427 |
| | | | 606/1 |
| 6,197,017 B1 | 3/2001 | Brock et al. | |
| 6,202,914 B1 | 3/2001 | Geiste et al. | |
| 6,241,139 B1 | 6/2001 | Milliman et al. | |
| 6,250,532 B1 | 6/2001 | Green et al. | |
| 6,264,086 B1 | 7/2001 | McGuckin, Jr. | |
| 6,264,087 B1 | 7/2001 | Whitman | |
| 6,269,977 B1 | 8/2001 | Moore | |
| 6,279,809 B1 | 8/2001 | Nicolo | |
| 6,315,183 B1 | 11/2001 | Piraka | |
| 6,315,184 B1 | 11/2001 | Whitman | |
| 6,325,810 B1 | 12/2001 | Hamilton et al. | |
| 6,330,965 B1 | 12/2001 | Milliman et al. | |
| 6,391,038 B2 | 5/2002 | Vargas et al. | |
| 6,398,797 B2 | 6/2002 | Bombard et al. | |
| 6,436,097 B1 | 8/2002 | Nardella | |
| 6,439,446 B1 | 8/2002 | Perry et al. | |
| 6,443,973 B1 | 9/2002 | Whitman | |
| 6,463,623 B2 | 10/2002 | Ahn et al. | |
| 6,478,804 B2 | 11/2002 | Vargas et al. | |
| 6,488,196 B1 | 12/2002 | Fenton, Jr. | |
| 6,503,257 B2 | 1/2003 | Grant et al. | |
| 6,505,768 B2 | 1/2003 | Whitman | |
| 6,544,274 B2 | 4/2003 | Danitz et al. | |
| 6,554,844 B2 | 4/2003 | Lee et al. | |
| 6,565,554 B1 | 5/2003 | Niemeyer | |
| 6,587,750 B2 | 7/2003 | Gerbi et al. | |
| 6,592,573 B2 | 7/2003 | Castaneda et al. | |
| 6,592,597 B2 | 7/2003 | Grant et al. | |
| 6,594,552 B1 | 7/2003 | Nowlin et al. | |
| 6,602,252 B2 | 8/2003 | Mollenauer | |
| 6,612,053 B2 | 9/2003 | Liao | |
| 6,619,529 B2 | 9/2003 | Green et al. | |
| D480,808 S | 10/2003 | Wells et al. | |
| 6,644,532 B2 | 11/2003 | Green et al. | |
| 6,656,193 B2 | 12/2003 | Grant et al. | |
| 6,666,854 B1 * | 12/2003 | Lange | A61B 17/2909 |
| | | | 606/1 |
| 6,669,073 B2 | 12/2003 | Milliman et al. | |
| 6,681,978 B2 | 1/2004 | Geiste et al. | |
| 6,698,643 B2 | 3/2004 | Whitman | |
| 6,716,232 B1 | 4/2004 | Vidal et al. | |
| 6,722,552 B2 | 4/2004 | Fenton, Jr. | |
| 6,731,473 B2 | 5/2004 | Li et al. | |
| 6,755,338 B2 | 6/2004 | Hahnen et al. | |
| 6,783,524 B2 | 8/2004 | Anderson et al. | |
| 6,786,382 B1 | 9/2004 | Hoffman | |
| 6,808,262 B2 | 10/2004 | Chapoy et al. | |
| 6,817,509 B2 | 11/2004 | Geiste et al. | |
| 6,830,174 B2 | 12/2004 | Hillstead et al. | |
| 6,835,199 B2 | 12/2004 | McGuckin, Jr. et al. | |
| 6,843,403 B2 | 1/2005 | Whitman | |
| RE38,708 E | 3/2005 | Bolanos et al. | |
| 6,877,647 B2 | 4/2005 | Green et al. | |
| 6,879,880 B2 | 4/2005 | Nowlin et al. | |
| 6,889,116 B2 | 5/2005 | Jinno | |
| 6,905,057 B2 | 6/2005 | Swayze et al. | |
| 6,953,138 B1 | 10/2005 | Dworak et al. | |
| 6,953,139 B2 | 10/2005 | Milliman et al. | |
| 6,958,036 B2 | 10/2005 | Seki et al. | |
| 6,959,852 B2 | 11/2005 | Shelton, IV et al. | |
| 6,962,594 B1 | 11/2005 | Thevenet | |
| 6,964,363 B2 | 11/2005 | Wales et al. | |
| 6,978,921 B2 | 12/2005 | Shelton, IV et al. | |
| 6,981,628 B2 | 1/2006 | Wales | |
| 6,986,451 B1 | 1/2006 | Mastri et al. | |
| 6,988,649 B2 | 1/2006 | Shelton, IV et al. | |
| 6,991,627 B2 | 1/2006 | Madhani et al. | |
| 6,994,714 B2 | 2/2006 | Vargas et al. | |
| 7,000,818 B2 | 2/2006 | Shelton, IV et al. | |
| 7,000,819 B2 | 2/2006 | Swayze et al. | |
| 7,032,799 B2 | 4/2006 | Viola et al. | |
| 7,044,352 B2 | 5/2006 | Shelton, IV et al. | |
| 7,044,353 B2 | 5/2006 | Mastri et al. | |
| 7,055,730 B2 | 6/2006 | Ehrenfels et al. | |
| 7,055,731 B2 | 6/2006 | Shelton, IV et al. | |
| 7,059,508 B2 | 6/2006 | Shelton, IV et al. | |
| 7,070,083 B2 | 7/2006 | Jankowski | |
| 7,083,075 B2 | 8/2006 | Swayze et al. | |
| 7,097,089 B2 | 8/2006 | Marczyk | |
| 7,111,769 B2 | 9/2006 | Wales et al. | |
| 7,114,642 B2 | 10/2006 | Whitman | |
| 7,121,446 B2 | 10/2006 | Arad et al. | |
| 7,128,253 B2 | 10/2006 | Mastri et al. | |
| 7,128,254 B2 | 10/2006 | Shelton, IV et al. | |
| 7,140,527 B2 | 11/2006 | Ehrenfels et al. | |
| 7,140,528 B2 | 11/2006 | Shelton, IV | |
| 7,143,923 B2 | 12/2006 | Shelton, IV et al. | |
| 7,143,924 B2 | 12/2006 | Scirica et al. | |
| 7,143,925 B2 | 12/2006 | Shelton, IV et al. | |
| 7,143,926 B2 | 12/2006 | Shelton, IV et al. | |
| 7,147,138 B2 | 12/2006 | Shelton, IV | |
| 7,159,750 B2 | 1/2007 | Racenet et al. | |
| 7,172,104 B2 | 2/2007 | Scirica et al. | |
| 7,188,758 B2 | 3/2007 | Viola et al. | |
| 7,207,471 B2 | 4/2007 | Heinrich et al. | |
| 7,213,736 B2 | 5/2007 | Wales et al. | |
| 7,225,963 B2 | 6/2007 | Scirica | |
| 7,225,964 B2 | 6/2007 | Mastri et al. | |
| 7,238,195 B2 | 7/2007 | Viola | |
| 7,246,734 B2 | 7/2007 | Shelton, IV | |
| 7,258,262 B2 | 8/2007 | Mastri et al. | |
| 7,267,682 B1 | 9/2007 | Bender et al. | |
| 7,278,562 B2 | 10/2007 | Mastri et al. | |
| 7,278,563 B1 | 10/2007 | Green | |
| 7,287,682 B1 | 10/2007 | Ezzat et al. | |
| 7,293,685 B2 | 11/2007 | Ehrenfels et al. | |
| 7,296,722 B2 | 11/2007 | Ivanko | |
| 7,296,724 B2 | 11/2007 | Green et al. | |
| 7,296,772 B2 | 11/2007 | Wang | |
| 7,300,444 B1 | 11/2007 | Nielsen et al. | |
| 7,303,108 B2 | 12/2007 | Shelton, IV | |
| 7,308,998 B2 | 12/2007 | Mastri et al. | |
| 7,326,232 B2 | 2/2008 | Viola et al. | |
| 7,328,828 B2 | 2/2008 | Ortiz et al. | |
| 7,328,829 B2 | 2/2008 | Arad et al. | |
| 7,334,717 B2 | 2/2008 | Rethy et al. | |
| 7,354,447 B2 | 4/2008 | Shelton, IV et al. | |
| 7,357,287 B2 | 4/2008 | Shelton, IV et al. | |
| 7,364,061 B2 | 4/2008 | Swayze et al. | |

(56) References Cited

U.S. PATENT DOCUMENTS

| | | | |
|---|---|---|---|
| 7,367,485 | B2 | 5/2008 | Shelton, IV et al. |
| 7,380,695 | B2 | 6/2008 | Doll et al. |
| 7,380,696 | B2 | 6/2008 | Shelton, IV et al. |
| 7,398,907 | B2 | 7/2008 | Racenet et al. |
| 7,399,310 | B2 | 7/2008 | Edoga et al. |
| 7,401,720 | B1 | 7/2008 | Durrani |
| 7,401,721 | B2 | 7/2008 | Holsten et al. |
| 7,404,508 | B2 | 7/2008 | Smith et al. |
| 7,404,509 | B2 | 7/2008 | Ortiz et al. |
| 7,407,074 | B2 | 8/2008 | Ortiz et al. |
| 7,407,075 | B2 | 8/2008 | Holsten et al. |
| 7,407,077 | B2 | 8/2008 | Ortiz et al. |
| 7,407,078 | B2 | 8/2008 | Shelton, IV et al. |
| 7,416,101 | B2 | 8/2008 | Shelton, IV et al. |
| 7,419,080 | B2 | 9/2008 | Smith et al. |
| 7,419,081 | B2 | 9/2008 | Ehrenfels et al. |
| 7,419,495 | B2 | 9/2008 | Menn et al. |
| 7,422,139 | B2 | 9/2008 | Shelton, IV et al. |
| 7,431,189 | B2 | 10/2008 | Shelton, IV et al. |
| 7,431,730 | B2 | 10/2008 | Viola |
| 7,434,715 | B2 | 10/2008 | Shelton, IV et al. |
| 7,434,717 | B2 | 10/2008 | Shelton, IV et al. |
| 7,438,208 | B2 | 10/2008 | Larson |
| 7,438,209 | B1 | 10/2008 | Hess et al. |
| 7,441,684 | B2 | 10/2008 | Shelton, IV et al. |
| 7,441,685 | B1 | 10/2008 | Boudreaux |
| 7,448,525 | B2 | 11/2008 | Shelton, IV et al. |
| 7,449,002 | B1 * | 11/2008 | Wenstad ......... A61M 25/09041 600/585 |
| 7,451,904 | B2 | 11/2008 | Shelton, IV |
| 7,455,208 | B2 | 11/2008 | Wales et al. |
| 7,455,676 | B2 | 11/2008 | Holsten et al. |
| 7,458,494 | B2 | 12/2008 | Matsutani et al. |
| 7,461,767 | B2 | 12/2008 | Viola et al. |
| 7,462,185 | B1 | 12/2008 | Knodel |
| 7,464,846 | B2 | 12/2008 | Shelton, IV et al. |
| 7,464,848 | B2 | 12/2008 | Green et al. |
| 7,464,849 | B2 | 12/2008 | Shelton, IV et al. |
| 7,467,740 | B2 | 12/2008 | Shelton, IV et al. |
| 7,472,814 | B2 | 1/2009 | Mastri et al. |
| 7,472,815 | B2 | 1/2009 | Shelton, IV et al. |
| 7,472,816 | B2 | 1/2009 | Holsten et al. |
| 7,473,258 | B2 | 1/2009 | Clauson et al. |
| 7,481,347 | B2 | 1/2009 | Roy |
| 7,481,348 | B2 | 1/2009 | Marczyk |
| 7,481,349 | B2 | 1/2009 | Holsten et al. |
| 7,487,899 | B2 | 2/2009 | Shelton, IV et al. |
| 7,490,749 | B2 | 2/2009 | Schall et al. |
| 7,494,039 | B2 * | 2/2009 | Racenet ................. A61B 34/71 227/180.1 |
| 7,500,979 | B2 | 3/2009 | Hueil et al. |
| 7,503,474 | B2 | 3/2009 | Hillstead et al. |
| 7,506,790 | B2 | 3/2009 | Shelton, IV |
| 7,510,107 | B2 | 3/2009 | Timm et al. |
| 7,513,408 | B2 | 4/2009 | Shelton, IV et al. |
| 7,517,356 | B2 | 4/2009 | Heinrich |
| 7,537,602 | B2 | 5/2009 | Whitman |
| 7,543,729 | B2 | 6/2009 | Ivanko |
| 7,543,730 | B1 | 6/2009 | Marczyk |
| 7,543,731 | B2 | 6/2009 | Green et al. |
| 7,556,185 | B2 | 7/2009 | Viola |
| 7,556,186 | B2 | 7/2009 | Milliman |
| 7,559,450 | B2 | 7/2009 | Wales et al. |
| 7,559,452 | B2 | 7/2009 | Wales et al. |
| 7,559,453 | B2 | 7/2009 | Heinrich et al. |
| 7,559,937 | B2 | 7/2009 | de la Torre et al. |
| 7,565,993 | B2 | 7/2009 | Milliman et al. |
| 7,568,603 | B2 | 8/2009 | Shelton, IV et al. |
| 7,568,604 | B2 | 8/2009 | Ehrenfels et al. |
| 7,571,845 | B2 | 8/2009 | Viola |
| 7,575,144 | B2 | 8/2009 | Ortiz et al. |
| 7,584,880 | B2 | 9/2009 | Racenet et al. |
| 7,588,174 | B2 | 9/2009 | Holsten et al. |
| 7,588,175 | B2 | 9/2009 | Timm et al. |
| 7,588,176 | B2 | 9/2009 | Timm et al. |
| 7,588,177 | B2 | 9/2009 | Racenet |
| 7,588,536 | B2 | 9/2009 | Peszynski |
| 7,597,229 | B2 | 10/2009 | Boudreaux et al. |
| 7,597,230 | B2 | 10/2009 | Racenet et al. |
| 7,604,150 | B2 | 10/2009 | Boudreaux |
| 7,604,151 | B2 | 10/2009 | Hess et al. |
| 7,607,557 | B2 | 10/2009 | Shelton, IV et al. |
| 7,611,038 | B2 | 11/2009 | Racenet et al. |
| 7,617,961 | B2 | 11/2009 | Viola |
| 7,624,902 | B2 | 12/2009 | Marczyk et al. |
| 7,624,903 | B2 | 12/2009 | Green et al. |
| 7,631,793 | B2 | 12/2009 | Rethy et al. |
| 7,631,794 | B2 | 12/2009 | Rethy et al. |
| 7,635,073 | B2 | 12/2009 | Heinrich |
| 7,635,074 | B2 | 12/2009 | Olson et al. |
| 7,635,373 | B2 | 12/2009 | Ortiz |
| 7,637,409 | B2 | 12/2009 | Marczyk |
| 7,637,410 | B2 | 12/2009 | Marczyk |
| 7,641,091 | B2 | 1/2010 | Olson et al. |
| 7,641,093 | B2 | 1/2010 | Doll et al. |
| 7,641,095 | B2 | 1/2010 | Viola |
| 7,644,848 | B2 | 1/2010 | Swayze et al. |
| 7,648,055 | B2 | 1/2010 | Marczyk |
| 7,648,519 | B2 * | 1/2010 | Lee ..................... A61B 17/2909 606/205 |
| 7,651,017 | B2 | 1/2010 | Ortiz et al. |
| 7,654,431 | B2 | 2/2010 | Hueil et al. |
| 7,658,311 | B2 | 2/2010 | Boudreaux |
| 7,658,312 | B2 | 2/2010 | Vidal et al. |
| 7,665,646 | B2 | 2/2010 | Prommersberger |
| 7,665,647 | B2 | 2/2010 | Shelton, IV et al. |
| 7,669,746 | B2 | 3/2010 | Shelton, IV |
| 7,670,334 | B2 | 3/2010 | Hueil et al. |
| 7,673,780 | B2 | 3/2010 | Shelton, IV et al. |
| 7,673,781 | B2 | 3/2010 | Swayze et al. |
| 7,673,782 | B2 | 3/2010 | Hess et al. |
| 7,673,783 | B2 | 3/2010 | Morgan et al. |
| 7,678,121 | B1 | 3/2010 | Knodel |
| 7,681,772 | B2 | 3/2010 | Green et al. |
| 7,682,367 | B2 | 3/2010 | Shah et al. |
| 7,682,368 | B1 | 3/2010 | Bombard et al. |
| 7,690,547 | B2 | 4/2010 | Racenet et al. |
| 7,694,865 | B2 | 4/2010 | Scirica |
| 7,699,205 | B2 | 4/2010 | Ivanko |
| 7,721,933 | B2 | 5/2010 | Ehrenfels et al. |
| 7,726,538 | B2 | 6/2010 | Holsten et al. |
| 7,726,539 | B2 | 6/2010 | Holsten et al. |
| 7,740,160 | B2 | 6/2010 | Viola |
| 7,744,628 | B2 | 6/2010 | Viola |
| 7,757,924 | B2 | 7/2010 | Gerbi et al. |
| 7,757,925 | B2 | 7/2010 | Viola et al. |
| 7,762,445 | B2 | 7/2010 | Heinrich et al. |
| 7,766,209 | B2 | 8/2010 | Baxter, III et al. |
| 7,766,210 | B2 | 8/2010 | Shelton, IV et al. |
| 7,766,924 | B1 | 8/2010 | Bombard et al. |
| 7,766,928 | B2 | 8/2010 | Ezzat et al. |
| 7,770,774 | B2 | 8/2010 | Mastri et al. |
| 7,770,775 | B2 | 8/2010 | Shelton, IV et al. |
| 7,771,416 | B2 | 8/2010 | Spivey et al. |
| 7,776,060 | B2 | 8/2010 | Mooradian et al. |
| 7,780,055 | B2 | 8/2010 | Scirica et al. |
| 7,784,662 | B2 | 8/2010 | Wales et al. |
| 7,789,283 | B2 | 9/2010 | Shah |
| 7,793,812 | B2 | 9/2010 | Moore et al. |
| 7,793,814 | B2 | 9/2010 | Racenet et al. |
| 7,794,475 | B2 | 9/2010 | Hess et al. |
| 7,798,386 | B2 | 9/2010 | Schall et al. |
| 7,799,039 | B2 | 9/2010 | Shelton, IV et al. |
| 7,810,690 | B2 | 10/2010 | Bilotti et al. |
| 7,810,692 | B2 | 10/2010 | Hall et al. |
| 7,810,693 | B2 | 10/2010 | Broehl et al. |
| 7,815,091 | B2 | 10/2010 | Marczyk |
| 7,815,092 | B2 | 10/2010 | Whitman et al. |
| 7,819,296 | B2 | 10/2010 | Hueil et al. |
| 7,819,297 | B2 | 10/2010 | Doll et al. |
| 7,819,298 | B2 | 10/2010 | Hall et al. |
| 7,819,299 | B2 | 10/2010 | Shelton, IV et al. |
| 7,823,760 | B2 | 11/2010 | Zemlok et al. |
| 7,824,426 | B2 | 11/2010 | Racenet et al. |

(56) References Cited

U.S. PATENT DOCUMENTS

| | | |
|---|---|---|
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,612 B2 | 11/2010 | Baxter, III et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,842,028 B2 | 11/2010 | Lee |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,881,809 B2 | 2/2011 | Rashidi |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,918,276 B2 | 4/2011 | Guignard et al. |
| 7,922,061 B2 | 4/2011 | Shelton, IV et al. |
| 7,922,063 B2 | 4/2011 | Zemlok et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,028,882 B2 | 10/2011 | Viola |
| 8,028,883 B2 | 10/2011 | Stopek |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,333,780 B1 | 12/2012 | Pedros et al. |
| 8,574,263 B2 | 11/2013 | Mueller |
| 8,603,135 B2 * | 12/2013 | Mueller .............. A61B 18/1445 606/205 |
| 8,783,542 B2 * | 7/2014 | Riestenberg ...... A61B 17/00491 227/176.1 |
| 8,888,775 B2 * | 11/2014 | Nau, Jr. .............. A61B 18/1445 606/49 |
| 2003/0074014 A1 * | 4/2003 | Castaneda ...... A61B 17/320016 606/167 |
| 2003/0092965 A1 | 5/2003 | Konomura et al. |
| 2004/0007608 A1 | 1/2004 | Ehrenfels et al. |
| 2004/0050902 A1 * | 3/2004 | Green .............. A61B 17/07207 227/176.1 |
| 2004/0059191 A1 | 3/2004 | Krupa et al. |
| 2004/0093029 A1 | 5/2004 | Zubik et al. |
| 2004/0094597 A1 | 5/2004 | Whitman et al. |
| 2004/0108357 A1 | 6/2004 | Milliman et al. |
| 2004/0149802 A1 | 8/2004 | Whitman |
| 2004/0173659 A1 | 9/2004 | Green et al. |
| 2004/0199180 A1 | 10/2004 | Knodel et al. |
| 2004/0199181 A1 | 10/2004 | Knodel et al. |
| 2004/0232199 A1 | 11/2004 | Shelton et al. |
| 2004/0232200 A1 | 11/2004 | Shelton et al. |
| 2004/0232201 A1 | 11/2004 | Wenchell et al. |
| 2004/0243151 A1 | 12/2004 | Demmy et al. |
| 2004/0267310 A1 | 12/2004 | Racenet et al. |
| 2004/0267311 A1 | 12/2004 | Viola et al. |
| 2005/0006429 A1 | 1/2005 | Wales et al. |
| 2005/0006430 A1 | 1/2005 | Wales |
| 2005/0006431 A1 | 1/2005 | Shelton et al. |
| 2005/0006432 A1 * | 1/2005 | Racenet .............. A61B 17/105 227/176.1 |
| 2005/0006433 A1 | 1/2005 | Milliman et al. |
| 2005/0006434 A1 * | 1/2005 | Wales .............. A61B 17/07207 227/19 |
| 2005/0023324 A1 | 2/2005 | Doll et al. |
| 2005/0023325 A1 | 2/2005 | Gresham et al. |
| 2005/0067457 A1 | 3/2005 | Shelton et al. |
| 2005/0067458 A1 | 3/2005 | Swayze et al. |
| 2005/0067459 A1 | 3/2005 | Swayze et al. |
| 2005/0067460 A1 | 3/2005 | Milliman et al. |
| 2005/0070925 A1 | 3/2005 | Shelton et al. |
| 2005/0070958 A1 | 3/2005 | Swayze et al. |
| 2005/0072827 A1 | 4/2005 | Mollenauer |
| 2005/0082336 A1 | 4/2005 | Ivanko |
| 2005/0103819 A1 | 5/2005 | Racenet et al. |
| 2005/0119669 A1 | 6/2005 | Demmy |
| 2005/0127131 A1 | 6/2005 | Mastri et al. |
| 2005/0145671 A1 | 7/2005 | Viola |
| 2005/0159778 A1 | 7/2005 | Heinrich et al. |
| 2005/0165415 A1 | 7/2005 | Wales |

(56) References Cited

U.S. PATENT DOCUMENTS

| | | |
|---|---|---|
| 2005/0173490 A1 | 8/2005 | Shelton |
| 2005/0178813 A1 | 8/2005 | Swayze et al. |
| 2005/0184121 A1 | 8/2005 | Heinrich |
| 2005/0184123 A1 | 8/2005 | Scirica |
| 2005/0184124 A1 | 8/2005 | Scirica et al. |
| 2005/0184125 A1 | 8/2005 | Marczyk |
| 2005/0184126 A1 | 8/2005 | Green et al. |
| 2005/0189397 A1 | 9/2005 | Jankowski |
| 2005/0192628 A1 | 9/2005 | Viola |
| 2005/0216055 A1 | 9/2005 | Scirica et al. |
| 2005/0230453 A1 | 10/2005 | Viola |
| 2005/0256452 A1 | 11/2005 | DeMarchi et al. |
| 2005/0263562 A1 | 12/2005 | Shelton et al. |
| 2005/0279804 A1 | 12/2005 | Scirica et al. |
| 2006/0000867 A1 | 1/2006 | Shelton et al. |
| 2006/0000868 A1 | 1/2006 | Shelton et al. |
| 2006/0011699 A1 | 1/2006 | Olson et al. |
| 2006/0016853 A1 | 1/2006 | Racenet |
| 2006/0022014 A1 | 2/2006 | Shelton et al. |
| 2006/0022015 A1 | 2/2006 | Shelton et al. |
| 2006/0025809 A1 | 2/2006 | Shelton |
| 2006/0043147 A1 | 3/2006 | Mastri et al. |
| 2006/0049229 A1 | 3/2006 | Milliman et al. |
| 2006/0049230 A1 | 3/2006 | Shelton et al. |
| 2006/0060630 A1 | 3/2006 | Shelton et al. |
| 2006/0081678 A1 | 4/2006 | Ehrenfels et al. |
| 2006/0097026 A1 | 5/2006 | Shelton |
| 2006/0124688 A1 | 6/2006 | Racenet et al. |
| 2006/0124689 A1 | 6/2006 | Arad et al. |
| 2006/0138193 A1 | 6/2006 | Viola et al. |
| 2006/0138194 A1 | 6/2006 | Viola et al. |
| 2006/0151567 A1 | 7/2006 | Roy |
| 2006/0151568 A1 | 7/2006 | Weller et al. |
| 2006/0151569 A1 | 7/2006 | Ehrenfels et al. |
| 2006/0175375 A1 | 8/2006 | Shelton et al. |
| 2006/0180634 A1 | 8/2006 | Shelton et al. |
| 2006/0201990 A1 | 9/2006 | Mastri et al. |
| 2006/0201991 A1 | 9/2006 | Mastri et al. |
| 2006/0226195 A1 | 10/2006 | Scirica et al. |
| 2006/0226196 A1 | 10/2006 | Hueil et al. |
| 2006/0252993 A1* | 11/2006 | Freed ............... A61M 25/0147 604/95.04 |
| 2006/0255090 A1 | 11/2006 | Milliman et al. |
| 2006/0278680 A1 | 12/2006 | Viola et al. |
| 2006/0278681 A1 | 12/2006 | Viola et al. |
| 2006/0289600 A1 | 12/2006 | Wales et al. |
| 2006/0289602 A1 | 12/2006 | Wales et al. |
| 2007/0021737 A1* | 1/2007 | Lee ................... A61B 17/22 606/1 |
| 2007/0023477 A1 | 2/2007 | Whitman et al. |
| 2007/0027469 A1 | 2/2007 | Smith et al. |
| 2007/0034669 A1 | 2/2007 | de la Torre et al. |
| 2007/0034670 A1 | 2/2007 | Racenet et al. |
| 2007/0045379 A1 | 3/2007 | Shelton |
| 2007/0045380 A1 | 3/2007 | Mastri et al. |
| 2007/0068989 A1 | 3/2007 | Shelton |
| 2007/0068990 A1 | 3/2007 | Shelton et al. |
| 2007/0073340 A1 | 3/2007 | Shelton et al. |
| 2007/0073341 A1 | 3/2007 | Smith et al. |
| 2007/0075114 A1 | 4/2007 | Shelton et al. |
| 2007/0075115 A1 | 4/2007 | Olson et al. |
| 2007/0075116 A1 | 4/2007 | Whitman |
| 2007/0083233 A1 | 4/2007 | Ortiz et al. |
| 2007/0083234 A1 | 4/2007 | Shelton et al. |
| 2007/0084896 A1 | 4/2007 | Doll et al. |
| 2007/0084897 A1 | 4/2007 | Shelton et al. |
| 2007/0084898 A1* | 4/2007 | Scirica ............ A61B 17/07207 227/176.1 |
| 2007/0084899 A1 | 4/2007 | Taylor |
| 2007/0102472 A1 | 5/2007 | Shelton |
| 2007/0102473 A1 | 5/2007 | Shelton et al. |
| 2007/0102474 A1 | 5/2007 | Shelton et al. |
| 2007/0102475 A1 | 5/2007 | Ortiz et al. |
| 2007/0102476 A1 | 5/2007 | Shelton et al. |
| 2007/0106317 A1 | 5/2007 | Shelton et al. |
| 2007/0108252 A1 | 5/2007 | Racenet et al. |
| 2007/0114261 A1 | 5/2007 | Ortiz et al. |
| 2007/0114262 A1 | 5/2007 | Mastri et al. |
| 2007/0119900 A1 | 5/2007 | Ehrenfels et al. |
| 2007/0119901 A1 | 5/2007 | Ehrenfels et al. |
| 2007/0125826 A1 | 6/2007 | Shelton |
| 2007/0125827 A1 | 6/2007 | Viola |
| 2007/0125828 A1 | 6/2007 | Rethy et al. |
| 2007/0145095 A1 | 6/2007 | Heinrich et al. |
| 2007/0145096 A1 | 6/2007 | Viola et al. |
| 2007/0152014 A1 | 7/2007 | Gillum et al. |
| 2007/0158385 A1 | 7/2007 | Hueil et al. |
| 2007/0170225 A1 | 7/2007 | Shelton et al. |
| 2007/0175947 A1 | 8/2007 | Ortiz et al. |
| 2007/0175948 A1* | 8/2007 | Scirica ............ A61B 17/07207 227/175.1 |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175952 A1 | 8/2007 | Shelton et al. |
| 2007/0175953 A1 | 8/2007 | Shelton et al. |
| 2007/0175954 A1 | 8/2007 | Viola |
| 2007/0175955 A1 | 8/2007 | Shelton et al. |
| 2007/0175956 A1 | 8/2007 | Swayze et al. |
| 2007/0175957 A1 | 8/2007 | Shelton et al. |
| 2007/0175958 A1 | 8/2007 | Shelton et al. |
| 2007/0175959 A1 | 8/2007 | Shelton et al. |
| 2007/0175960 A1 | 8/2007 | Shelton et al. |
| 2007/0175961 A1 | 8/2007 | Shelton et al. |
| 2007/0175962 A1 | 8/2007 | Shelton et al. |
| 2007/0175964 A1 | 8/2007 | Shelton et al. |
| 2007/0179528 A1 | 8/2007 | Soltz et al. |
| 2007/0187453 A1 | 8/2007 | Smith et al. |
| 2007/0187454 A1 | 8/2007 | Scirica |
| 2007/0187455 A1 | 8/2007 | Demmy et al. |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0221700 A1 | 9/2007 | Ortiz et al. |
| 2007/0221701 A1 | 9/2007 | Ortiz et al. |
| 2007/0225562 A1 | 9/2007 | Spivey et al. |
| 2007/0250113 A1* | 10/2007 | Hegeman ............ H04W 24/08 606/207 |
| 2007/0276430 A1* | 11/2007 | Lee .................... A61B 1/00071 606/205 |
| 2007/0278277 A1 | 12/2007 | Wixey et al. |
| 2007/0282371 A1* | 12/2007 | Lee ....................... A61B 17/29 606/205 |
| 2007/0295780 A1 | 12/2007 | Shelton et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0048002 A1 | 2/2008 | Smith et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0110958 A1 | 5/2008 | McKenna et al. |
| 2008/0110961 A1 | 5/2008 | Voegele et al. |
| 2008/0125812 A1 | 5/2008 | Zubik et al. |
| 2008/0149685 A1 | 6/2008 | Smith et al. |
| 2008/0164296 A1 | 7/2008 | Shelton et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |

(56) References Cited

U.S. PATENT DOCUMENTS

| | | |
|---|---|---|
| 2008/0169333 A1 | 7/2008 | Shelton et al. |
| 2008/0188868 A1 | 8/2008 | Weitzner et al. |
| 2008/0210738 A1 | 9/2008 | Shelton et al. |
| 2008/0223903 A1 | 9/2008 | Marczyk |
| 2008/0237296 A1 | 10/2008 | Boudreaux et al. |
| 2008/0237298 A1 | 10/2008 | Schall et al. |
| 2008/0277447 A1 | 11/2008 | Smith et al. |
| 2008/0283570 A1 | 11/2008 | Boyden et al. |
| 2008/0283571 A1 | 11/2008 | Boyden et al. |
| 2008/0283572 A1 | 11/2008 | Boyden et al. |
| 2008/0283574 A1 | 11/2008 | Boyden et al. |
| 2008/0283576 A1 | 11/2008 | Boyden et al. |
| 2008/0283577 A1 | 11/2008 | Boyden et al. |
| 2008/0287987 A1 | 11/2008 | Boyden et al. |
| 2008/0296343 A1 | 12/2008 | Schall et al. |
| 2008/0296344 A1 | 12/2008 | Cropper et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0302854 A1 | 12/2008 | Rethy et al. |
| 2008/0308601 A1 | 12/2008 | Timm et al. |
| 2008/0308602 A1 | 12/2008 | Timm et al. |
| 2008/0308603 A1 | 12/2008 | Shelton et al. |
| 2008/0308604 A1 | 12/2008 | Timm et al. |
| 2008/0308606 A1 | 12/2008 | Timm et al. |
| 2008/0308607 A1 | 12/2008 | Timm et al. |
| 2008/0314954 A1 | 12/2008 | Boudreaux |
| 2008/0314955 A1 | 12/2008 | Boudreaux et al. |
| 2008/0314957 A1 | 12/2008 | Boudreaux |
| 2008/0314961 A1 | 12/2008 | Boudreaux et al. |
| 2008/0314962 A1 | 12/2008 | Boudreaux |
| 2009/0001121 A1 | 1/2009 | Hess et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001130 A1 | 1/2009 | Hess et al. |
| 2009/0005808 A1 | 1/2009 | Hess et al. |
| 2009/0008424 A1 | 1/2009 | Green |
| 2009/0054671 A1 | 2/2009 | Racenet et al. |
| 2009/0054728 A1 | 2/2009 | Trusty |
| 2009/0054734 A1 | 2/2009 | DeSantis et al. |
| 2009/0057370 A1 | 3/2009 | Marczyk et al. |
| 2009/0065549 A1* | 3/2009 | Viola ............... A61B 17/10 606/205 |
| 2009/0065550 A1 | 3/2009 | Green et al. |
| 2009/0065551 A1 | 3/2009 | Green et al. |
| 2009/0078738 A1 | 3/2009 | Racenet et al. |
| 2009/0078739 A1 | 3/2009 | Viola |
| 2009/0084826 A1 | 4/2009 | Shah et al. |
| 2009/0088792 A1 | 4/2009 | Hoell, Jr. et al. |
| 2009/0090763 A1 | 4/2009 | Zemlok et al. |
| 2009/0090764 A1* | 4/2009 | Viola ............... A61B 17/07207 227/176.1 |
| 2009/0090765 A1 | 4/2009 | Blier et al. |
| 2009/0090766 A1 | 4/2009 | Knodel |
| 2009/0095790 A1 | 4/2009 | Whitman et al. |
| 2009/0101692 A1 | 4/2009 | Whitman et al. |
| 2009/0101694 A1 | 4/2009 | Marczyk |
| 2009/0105535 A1 | 4/2009 | Green et al. |
| 2009/0108048 A1 | 4/2009 | Zemlok et al. |
| 2009/0108049 A1 | 4/2009 | Roy |
| 2009/0114699 A1 | 5/2009 | Viola |
| 2009/0114700 A1 | 5/2009 | Marczyk |
| 2009/0114701 A1 | 5/2009 | Zemlok et al. |
| 2009/0134199 A1 | 5/2009 | Heinrich et al. |
| 2009/0198272 A1* | 8/2009 | Kerver ............... A61B 17/29 606/205 |
| 2009/0206124 A1* | 8/2009 | Hall ............... A61B 17/115 227/175.1 |
| 2009/0209946 A1 | 8/2009 | Swayze et al. |
| 2009/0209990 A1 | 8/2009 | Yates et al. |
| 2009/0218384 A1 | 9/2009 | Aranyi |
| 2009/0234280 A1 | 9/2009 | Tah et al. |
| 2009/0236393 A1 | 9/2009 | Viola |
| 2009/0236395 A1 | 9/2009 | Scirica |
| 2009/0242610 A1 | 10/2009 | Shelton, IV et al. |
| 2009/0242611 A1 | 10/2009 | Hathaway et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0261142 A1 | 10/2009 | Milliman et al. |
| 2009/0261144 A1 | 10/2009 | Sniffin et al. |
| 2009/0261145 A1 | 10/2009 | Heinrich et al. |
| 2009/0266868 A1 | 10/2009 | Wenchell et al. |
| 2009/0272784 A1 | 11/2009 | Farascioni |
| 2009/0272787 A1 | 11/2009 | Scirica |
| 2009/0277946 A1 | 11/2009 | Marczyk |
| 2009/0277947 A1 | 11/2009 | Viola |
| 2009/0277949 A1 | 11/2009 | Viola et al. |
| 2009/0283568 A1 | 11/2009 | Racenet et al. |
| 2009/0289096 A1 | 11/2009 | Shelton, IV et al. |
| 2009/0302090 A1 | 12/2009 | Shah |
| 2009/0302091 A1 | 12/2009 | Shah |
| 2009/0306708 A1 | 12/2009 | Shah |
| 2009/0308907 A1 | 12/2009 | Nalagatla et al. |
| 2009/0308908 A1 | 12/2009 | Green et al. |
| 2009/0308909 A1 | 12/2009 | Nalagatla et al. |
| 2009/0312773 A1* | 12/2009 | Cabrera ............ A61B 17/0469 606/144 |
| 2009/0314820 A1 | 12/2009 | Green et al. |
| 2009/0314821 A1 | 12/2009 | Racenet |
| 2010/0001036 A1 | 1/2010 | Marczyk et al. |
| 2010/0004633 A1* | 1/2010 | Rothe ............... A61M 25/0136 604/528 |
| 2010/0006620 A1 | 1/2010 | Sorrentino et al. |
| 2010/0010512 A1* | 1/2010 | Taylor ............ A61B 17/0491 606/144 |
| 2010/0012702 A1 | 1/2010 | Marczyk |
| 2010/0012703 A1 | 1/2010 | Calabrese et al. |
| 2010/0012704 A1 | 1/2010 | Tarinelli Racenet et al. |
| 2010/0025452 A1 | 2/2010 | Whitman |
| 2010/0030018 A1* | 2/2010 | Fortier ............ A61B 18/1445 600/104 |
| 2010/0032470 A1 | 2/2010 | Hess et al. |
| 2010/0044411 A1 | 2/2010 | Viola |
| 2010/0065605 A1 | 3/2010 | Shelton, VI et al. |
| 2010/0065606 A1 | 3/2010 | Stopek |
| 2010/0065608 A1 | 3/2010 | Olson et al. |
| 2010/0069834 A1* | 3/2010 | Schultz ............ A61M 25/0147 604/95.04 |
| 2010/0069942 A1 | 3/2010 | Shelton, IV |
| 2010/0072251 A1 | 3/2010 | Baxter, III et al. |
| 2010/0072252 A1 | 3/2010 | Baxter, III |
| 2010/0072253 A1 | 3/2010 | Baxter, III et al. |
| 2010/0072254 A1 | 3/2010 | Aranyi et al. |
| 2010/0072255 A1 | 3/2010 | Olson et al. |
| 2010/0072256 A1 | 3/2010 | Baxter, III et al. |
| 2010/0072258 A1 | 3/2010 | Farascioni et al. |
| 2010/0076260 A1 | 3/2010 | Taylor et al. |
| 2010/0076429 A1 | 3/2010 | Heinrich |
| 2010/0076459 A1 | 3/2010 | Farascioni |
| 2010/0076460 A1* | 3/2010 | Taylor ............ A61B 17/0491 606/144 |
| 2010/0089970 A1 | 4/2010 | Smith et al. |
| 2010/0089972 A1 | 4/2010 | Marczyk |
| 2010/0089974 A1 | 4/2010 | Shelton, IV |
| 2010/0096432 A1 | 4/2010 | Scirica |
| 2010/0096433 A1 | 4/2010 | Mastri et al. |
| 2010/0096434 A1 | 4/2010 | Viola et al. |
| 2010/0108739 A1 | 5/2010 | Holsten et al. |
| 2010/0116867 A1 | 5/2010 | Balbierz et al. |
| 2010/0116868 A1 | 5/2010 | Prommersberger |
| 2010/0121147 A1 | 5/2010 | Oskin et al. |
| 2010/0127040 A1 | 5/2010 | Smith et al. |
| 2010/0127041 A1 | 5/2010 | Morgan et al. |
| 2010/0127042 A1 | 5/2010 | Shelton, IV |
| 2010/0127043 A1 | 5/2010 | Olson et al. |
| 2010/0133317 A1 | 6/2010 | Shelton, IV et al. |
| 2010/0133318 A1 | 6/2010 | Boudreaux |
| 2010/0133319 A1 | 6/2010 | Milliman et al. |
| 2010/0133321 A1 | 6/2010 | Racenet et al. |
| 2010/0147921 A1 | 6/2010 | Olson |

(56) References Cited

U.S. PATENT DOCUMENTS

| | | | |
|---|---|---|---|
| 2010/0147922 | A1 | 6/2010 | Olson |
| 2010/0155453 | A1 | 6/2010 | Bombard et al. |
| 2010/0163596 | A1 | 7/2010 | Marczyk |
| 2010/0163597 | A1 | 7/2010 | Shah et al. |
| 2010/0170931 | A1 | 7/2010 | Viola |
| 2010/0170933 | A1 | 7/2010 | Ivanko |
| 2010/0179540 | A1* | 7/2010 | Marczyk .......... A61B 18/1445 606/41 |
| 2010/0193566 | A1 | 8/2010 | Scheib et al. |
| 2010/0224668 | A1 | 9/2010 | Fontayne et al. |
| 2010/0230468 | A1 | 9/2010 | Viola |
| 2010/0237130 | A1 | 9/2010 | Scirica |
| 2010/0237131 | A1 | 9/2010 | Milliman et al. |
| 2010/0237133 | A1 | 9/2010 | Shah |
| 2010/0243706 | A1 | 9/2010 | Cohen et al. |
| 2010/0243707 | A1 | 9/2010 | Olson et al. |
| 2010/0243708 | A1 | 9/2010 | Aranyi et al. |
| 2010/0243709 | A1 | 9/2010 | Hess et al. |
| 2010/0243710 | A1 | 9/2010 | Mastri et al. |
| 2010/0243711 | A1 | 9/2010 | Olson et al. |
| 2010/0249497 | A1* | 9/2010 | Peine ............... A61B 17/2909 600/104 |
| 2010/0249802 | A1 | 9/2010 | May et al. |
| 2010/0252610 | A1 | 10/2010 | Viola |
| 2010/0252611 | A1 | 10/2010 | Ezzat et al. |
| 2010/0252612 | A1 | 10/2010 | Viola |
| 2010/0264192 | A1 | 10/2010 | Marczyk |
| 2010/0264193 | A1 | 10/2010 | Huang et al. |
| 2010/0264194 | A1 | 10/2010 | Huang et al. |
| 2010/0270356 | A1 | 10/2010 | Holsten et al. |
| 2010/0282816 | A1 | 11/2010 | Scirica et al. |
| 2010/0282817 | A1 | 11/2010 | Ehrenfels et al. |
| 2010/0282819 | A1 | 11/2010 | Racenet et al. |
| 2010/0294828 | A1 | 11/2010 | Bindra et al. |
| 2010/0294829 | A1 | 11/2010 | Giordano et al. |
| 2010/0301095 | A1 | 12/2010 | Shelton, IV et al. |
| 2010/0301096 | A1 | 12/2010 | Moore et al. |
| 2010/0305552 | A1 | 12/2010 | Shelton, IV et al. |
| 2010/0308099 | A1* | 12/2010 | Marczyk .......... A61B 17/07207 227/175.1 |
| 2010/0308100 | A1 | 12/2010 | Boudreaux |
| 2010/0320252 | A1* | 12/2010 | Viola ............... A61B 17/068 227/176.1 |
| 2010/0320253 | A1 | 12/2010 | Marczyk |
| 2010/0320254 | A1 | 12/2010 | Zemlok et al. |
| 2011/0006099 | A1 | 1/2011 | Hall et al. |
| 2011/0006101 | A1 | 1/2011 | Hall et al. |
| 2011/0006103 | A1 | 1/2011 | Laurent et al. |
| 2011/0009863 | A1* | 1/2011 | Marczyk .......... A61B 18/1445 606/51 |
| 2011/0011914 | A1 | 1/2011 | Baxter, III et al. |
| 2011/0011915 | A1 | 1/2011 | Shelton, IV |
| 2011/0017801 | A1 | 1/2011 | Zemlok et al. |
| 2011/0024477 | A1 | 2/2011 | Hall |
| 2011/0024478 | A1 | 2/2011 | Shelton, IV |
| 2011/0024479 | A1 | 2/2011 | Swensgard et al. |
| 2011/0024480 | A1 | 2/2011 | Marczyk |
| 2011/0036887 | A1 | 2/2011 | Zemlok et al. |
| 2011/0036888 | A1 | 2/2011 | Pribanic et al. |
| 2011/0036890 | A1 | 2/2011 | Ma |
| 2011/0036891 | A1 | 2/2011 | Zemlok et al. |
| 2011/0036892 | A1 | 2/2011 | Marczyk et al. |
| 2011/0036893 | A1 | 2/2011 | Viola |
| 2011/0036895 | A1 | 2/2011 | Marczyk et al. |
| 2011/0040308 | A1* | 2/2011 | Cabrera ........... A61B 17/06166 606/144 |
| 2011/0042439 | A1 | 2/2011 | Johnson et al. |
| 2011/0042440 | A1 | 2/2011 | Holsten et al. |
| 2011/0042441 | A1 | 2/2011 | Shelton, IV et al. |
| 2011/0062212 | A1 | 3/2011 | Shelton, IV et al. |
| 2011/0062213 | A1 | 3/2011 | Scirica et al. |
| 2011/0068144 | A1 | 3/2011 | Krehel |
| 2011/0068145 | A1 | 3/2011 | Bedi et al. |
| 2011/0068146 | A1 | 3/2011 | Viola et al. |
| 2011/0068148 | A1 | 3/2011 | Hall et al. |
| 2011/0079626 | A1 | 4/2011 | Viola et al. |
| 2011/0079628 | A1 | 4/2011 | Racenet et al. |
| 2011/0084112 | A1 | 4/2011 | Kostrzewski |
| 2011/0084113 | A1 | 4/2011 | Bedi et al. |
| 2011/0084114 | A1 | 4/2011 | Marczyk et al. |
| 2011/0084115 | A1 | 4/2011 | Bedi et al. |
| 2011/0087276 | A1 | 4/2011 | Bedi et al. |
| 2011/0089220 | A1 | 4/2011 | Ingmanson et al. |
| 2011/0089221 | A1 | 4/2011 | Masiakos et al. |
| 2011/0095067 | A1 | 4/2011 | Ohdaira |
| 2011/0101066 | A1 | 5/2011 | Farascioni et al. |
| 2011/0101067 | A1 | 5/2011 | Johnson et al. |
| 2011/0101069 | A1 | 5/2011 | Bombard et al. |
| 2011/0101070 | A1 | 5/2011 | Bettuchi et al. |
| 2011/0106073 | A1* | 5/2011 | Mueller ........... A61B 18/1445 606/41 |
| 2011/0106078 | A1* | 5/2011 | Mueller ........... A61B 17/29 606/205 |
| 2011/0108603 | A1 | 5/2011 | Racenet et al. |
| 2011/0108605 | A1 | 5/2011 | Sapienza |
| 2011/0108606 | A1 | 5/2011 | Whitman |
| 2011/0114702 | A1 | 5/2011 | Farascioni |
| 2011/0121049 | A1 | 5/2011 | Malinouskas et al. |
| 2011/0121050 | A1 | 5/2011 | Nicholas et al. |
| 2011/0121051 | A1 | 5/2011 | Shelton, IV et al. |
| 2011/0121052 | A1 | 5/2011 | Shelton, IV et al. |
| 2011/0132960 | A1 | 6/2011 | Whitman et al. |
| 2011/0132961 | A1 | 6/2011 | Whitman et al. |
| 2011/0132962 | A1 | 6/2011 | Hall et al. |
| 2011/0132963 | A1 | 6/2011 | Giordano et al. |
| 2011/0132964 | A1 | 6/2011 | Weisenburgh, II et al. |
| 2011/0132965 | A1 | 6/2011 | Moore et al. |
| 2011/0139851 | A1 | 6/2011 | McCuen |
| 2011/0144576 | A1 | 6/2011 | Rothe et al. |
| 2011/0144640 | A1 | 6/2011 | Heinrich et al. |
| 2011/0147433 | A1 | 6/2011 | Shelton, IV et al. |
| 2011/0147434 | A1 | 6/2011 | Hueil et al. |
| 2011/0155780 | A1 | 6/2011 | Boudreaux |
| 2011/0155781 | A1 | 6/2011 | Swensgard et al. |
| 2011/0155784 | A1 | 6/2011 | Shelton, IV et al. |
| 2011/0155785 | A1 | 6/2011 | Laurent et al. |
| 2011/0155786 | A1 | 6/2011 | Shelton, IV |
| 2011/0155787 | A1 | 6/2011 | Baxter, III et al. |
| 2011/0155788 | A1 | 6/2011 | Hillstead et al. |
| 2011/0163146 | A1 | 7/2011 | Ortiz et al. |
| 2011/0163147 | A1 | 7/2011 | Laurent et al. |
| 2011/0163148 | A1 | 7/2011 | Wenchell et al. |
| 2011/0163149 | A1 | 7/2011 | Viola |
| 2011/0163150 | A1 | 7/2011 | Farascioni |
| 2011/0168756 | A1 | 7/2011 | Racenet et al. |
| 2011/0168757 | A1 | 7/2011 | Viola et al. |
| 2011/0168758 | A1 | 7/2011 | Mastri et al. |
| 2011/0168759 | A1 | 7/2011 | Prommersberger |
| 2011/0168760 | A1 | 7/2011 | Viola et al. |
| 2011/0174862 | A1 | 7/2011 | Shelton, IV et al. |
| 2011/0174863 | A1 | 7/2011 | Shelton, IV et al. |
| 2011/0180585 | A1 | 7/2011 | Czernik et al. |
| 2011/0180586 | A1 | 7/2011 | Shah |
| 2011/0184443 | A1 | 7/2011 | Tzakis et al. |
| 2011/0184459 | A1* | 7/2011 | Malkowski ....... A61B 18/1445 606/206 |
| 2011/0186614 | A1 | 8/2011 | Kasvikis |
| 2011/0192881 | A1 | 8/2011 | Balbierz et al. |
| 2011/0192882 | A1 | 8/2011 | Hess et al. |
| 2011/0192883 | A1 | 8/2011 | Whitman et al. |
| 2011/0192884 | A1 | 8/2011 | Whitman et al. |
| 2011/0198385 | A1 | 8/2011 | Whitman et al. |
| 2011/0198386 | A1 | 8/2011 | Viola |
| 2011/0204119 | A1* | 8/2011 | McCuen ........... A61B 17/07207 227/175.1 |
| 2011/0204120 | A1 | 8/2011 | Crainich |
| 2011/0208211 | A1* | 8/2011 | Whitfield ......... A61B 17/1285 606/142 |
| 2011/0210157 | A1 | 9/2011 | Knodel et al. |
| 2011/0213363 | A1* | 9/2011 | Cunningham ..... A61B 18/1445 606/41 |
| 2011/0215132 | A1 | 9/2011 | Aranyi et al. |
| 2011/0215133 | A1 | 9/2011 | Aranyi |

(56) References Cited

U.S. PATENT DOCUMENTS

| | | |
|---|---|---|
| 2011/0226837 A1 | 9/2011 | Baxter, III et al. |
| 2011/0233258 A1 | 9/2011 | Boudreaux |
| 2011/0233259 A1 | 9/2011 | Olson |
| 2011/0233260 A1 | 9/2011 | Milliman et al. |
| 2011/0240711 A1 | 10/2011 | Scirica |
| 2011/0240712 A1 | 10/2011 | Kostrzewski |
| 2011/0240713 A1 | 10/2011 | Scirica et al. |
| 2011/0240714 A1 | 10/2011 | Whitman et al. |
| 2011/0253765 A1 | 10/2011 | Nicholas et al. |
| 2011/0253766 A1 | 10/2011 | Baxter, III et al. |
| 2011/0257679 A1 | 10/2011 | Ishitsuki et al. |
| 2011/0290856 A1 | 12/2011 | Shelton, IV et al. |
| 2012/0109186 A1* | 5/2012 | Parrott ............... A61B 17/29 606/206 |
| 2012/0234893 A1 | 9/2012 | Schuckmann et al. |
| 2012/0239009 A1 | 9/2012 | Mollere et al. |
| 2012/0253326 A1* | 10/2012 | Kleyman ............. A61B 34/30 606/1 |
| 2013/0012929 A1* | 1/2013 | Malkowski ........... A61B 17/29 606/1 |
| 2013/0131593 A1* | 5/2013 | Selkee ................ A61M 25/09 604/95.04 |
| 2014/0039470 A1* | 2/2014 | Mueller ............ A61B 18/1445 606/1 |
| 2014/0114293 A1* | 4/2014 | Jeong .................. A61B 34/70 606/1 |
| 2014/0194893 A1* | 7/2014 | Jeong .................. A61B 34/70 606/130 |
| 2014/0275763 A1* | 9/2014 | King ................. A61B 1/00105 600/110 |

FOREIGN PATENT DOCUMENTS

| | | |
|---|---|---|
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0656188 A2 | 6/1995 |
| EP | 0666057 A2 | 8/1995 |
| EP | 0705571 A1 | 4/1996 |
| EP | 0760230 A1 | 3/1997 |
| FR | 2542188 A1 | 9/1984 |
| FR | 2660851 A1 | 10/1991 |
| FR | 2681775 A1 | 4/1993 |
| GB | 1352554 A | 5/1974 |
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| SU | 659146 A1 | 4/1979 |
| SU | 728848 A1 | 4/1980 |
| SU | 980703 | 12/1982 |
| SU | 980703 A1 | 12/1982 |
| SU | 990220 | 1/1983 |
| SU | 990220 A1 | 1/1983 |
| WO | 8302247 A1 | 7/1983 |
| WO | 2008302247 | 7/1983 |
| WO | 8910094 A1 | 11/1989 |
| WO | 9210976 A1 | 7/1992 |
| WO | 9308754 A1 | 5/1993 |
| WO | 9314706 A1 | 8/1993 |
| WO | 2008045333 A2 | 4/2008 |
| WO | WO-2008045333 A2 * | 4/2008 ............ A61B 17/04 |

\* cited by examiner

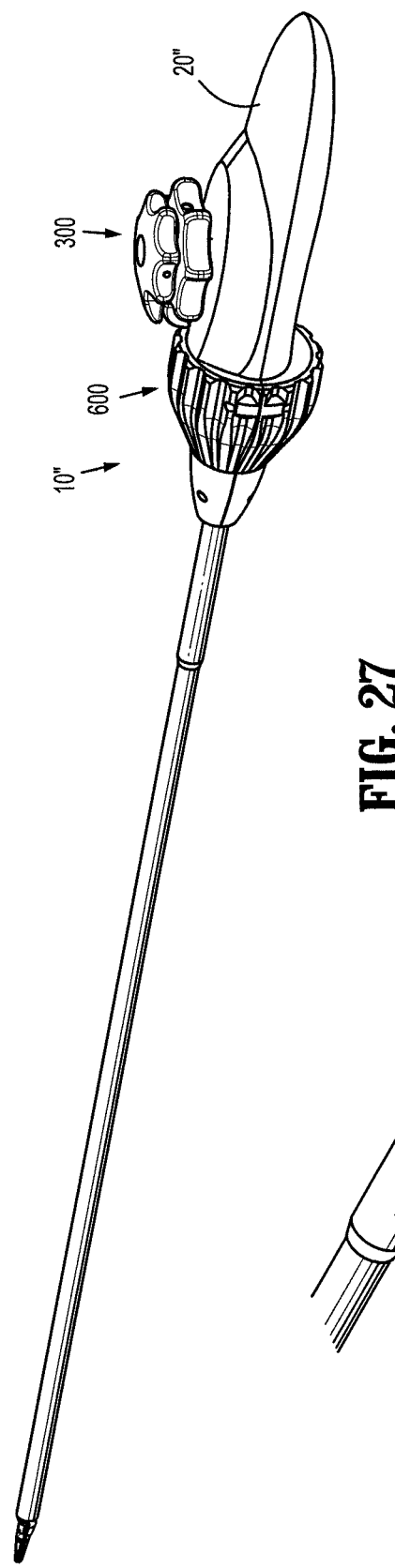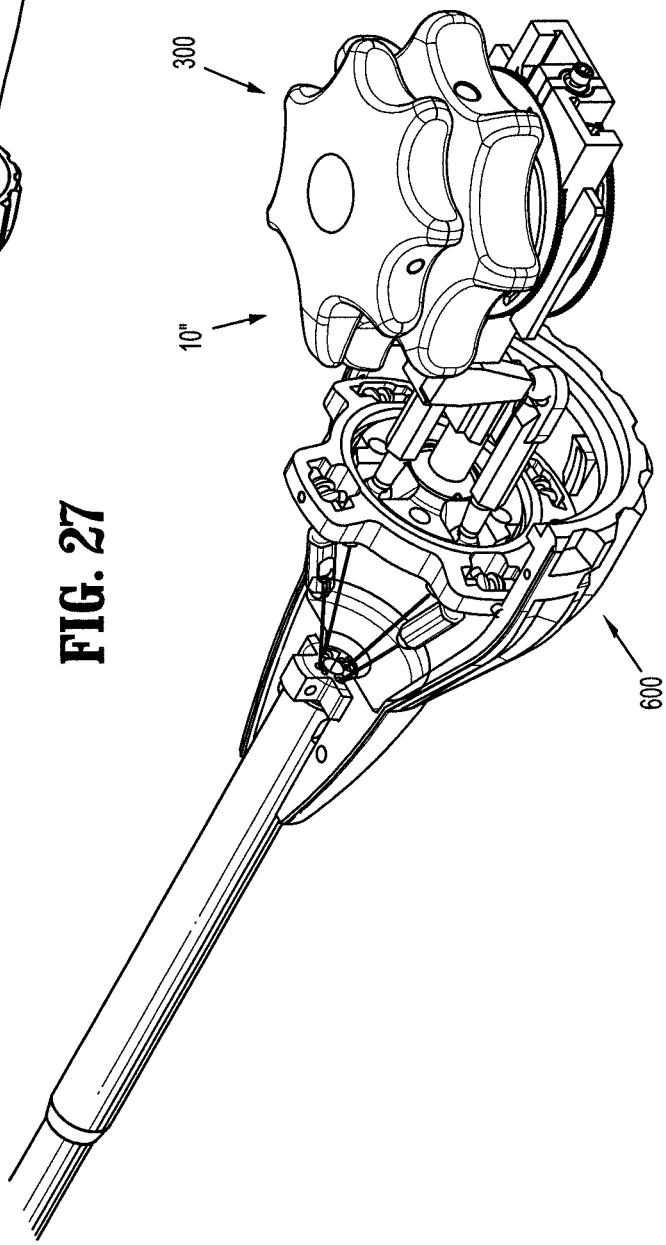
FIG. 27
FIG. 28

SURGICAL DEVICE WITH ARTICULATION AND WRIST ROTATION

CROSS-REFERENCE TO RELATED APPLICATIONS

This present application is a divisional of U.S. patent application Ser. No. 15/422,636 filed Feb. 2, 2017, which issued as U.S. Pat. No. 10,448,964, which is a continuation of U.S. patent application Ser. No. 13/543,931 filed on Jul. 9, 2012, now abandoned, which claims benefit of and priority to U.S. Provisional Application No. 61/505,604, filed Jul. 8, 2011, and the disclosures of each of the above-identified applications are hereby incorporated by reference in their entirety.

BACKGROUND

The present disclosure relates to a device for surgically manipulating tissue. More particularly, the present disclosure relates to a device for surgically joining and/or cutting tissue utilizing an elongated, generally flexible and articulating shaft.

TECHNICAL FIELD

Various types of surgical instruments used to surgically join tissue are known in the art, and are commonly used, for example, for closure of tissue or organs in transection, resection, anastomoses, for occlusion of organs in thoracic and abdominal procedures, and for electrosurgically fusing or sealing tissue.

One example of such a surgical instrument is a surgical stapling instrument, which may include an anvil assembly, a cartridge assembly for supporting an array of surgical staples, an approximation mechanism for approximating the cartridge and anvil assemblies, and a firing mechanism for ejecting the surgical staples from the cartridge assembly.

Using a surgical stapling instrument, it is common for a surgeon to approximate the anvil and cartridge members. Next, the surgeon can fire the instrument to emplace staples in tissue. Additionally, the surgeon may use the same instrument or a separate instrument to cut the tissue adjacent or between the row(s) of staples.

Another example of a surgical instrument used to surgically join tissue is an electrosurgical forceps, which utilize both mechanical clamping action and electrical energy to effect hemostasis by heating the tissue and blood vessels to coagulate, cauterize and/or seal tissue. As an alternative to open forceps for use with open surgical procedures, many modern surgeons use endoscopes and endoscopic instruments for remotely accessing organs through smaller, puncture-like incisions. As a direct result thereof, patients tend to benefit from less scarring and reduced healing time.

SUMMARY

The present disclosure relates to a surgical instrument comprising a handle assembly, an elongated shaft, an end effector, a rotation mechanism, and an articulation mechanism. The rotation mechanism is disposed in mechanical cooperation with the handle assembly and effects rotation of the end effector about the second longitudinal axis. The articulation mechanism is disposed in mechanical cooperation with the handle assembly and effects movement of the end effector from a first position where the first longitudinal axis is substantially aligned with the second longitudinal axis to a second position where the second longitudinal axis is displaced from the first longitudinal axis. The articulation mechanism comprises a first articulation control disposed in mechanical cooperation with the handle assembly, a first cable and a second cable. Actuation of the first articulation control in a first direction causes the first cable to move distally and causes the second cable to move proximally.

BRIEF DESCRIPTION OF THE DRAWINGS

Various embodiments of the presently disclosed surgical instrument are described herein with reference to the drawings wherein:

FIG. 27 is a perspective view of forceps according to a third embodiment of the present disclosure; and FIG. 28 is a perspective view of the handle portion of FIG. 27 with portions of the handle assembly removed.

DETAILED DESCRIPTION

Figure 1:
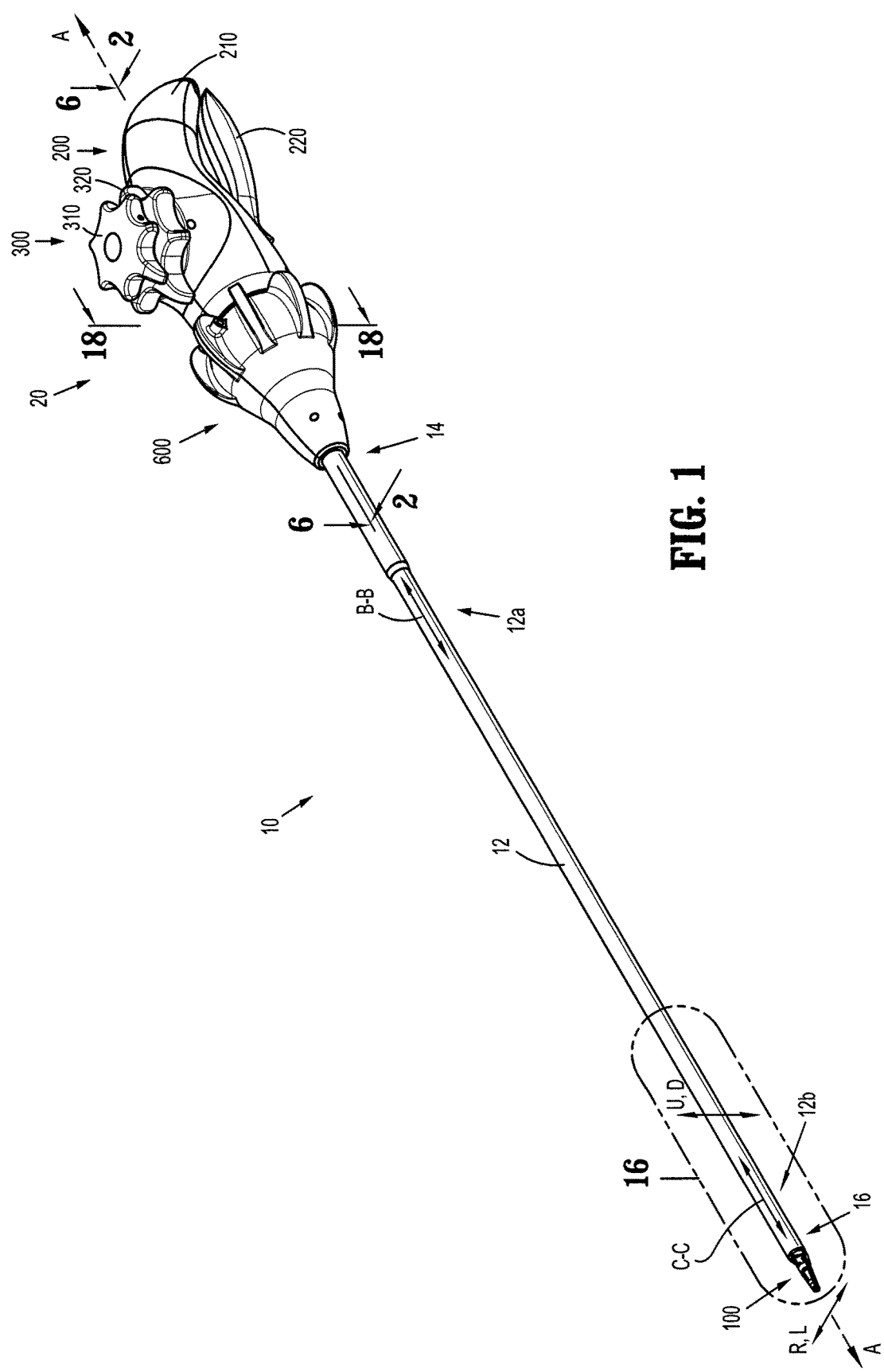
FIG. 1 is a perspective view of an endoscopic forceps depicting a handle assembly, a flexible shaft, an articulation assembly, a rotation assembly, and an end effector assembly according to the present disclosure.
Figure 2:
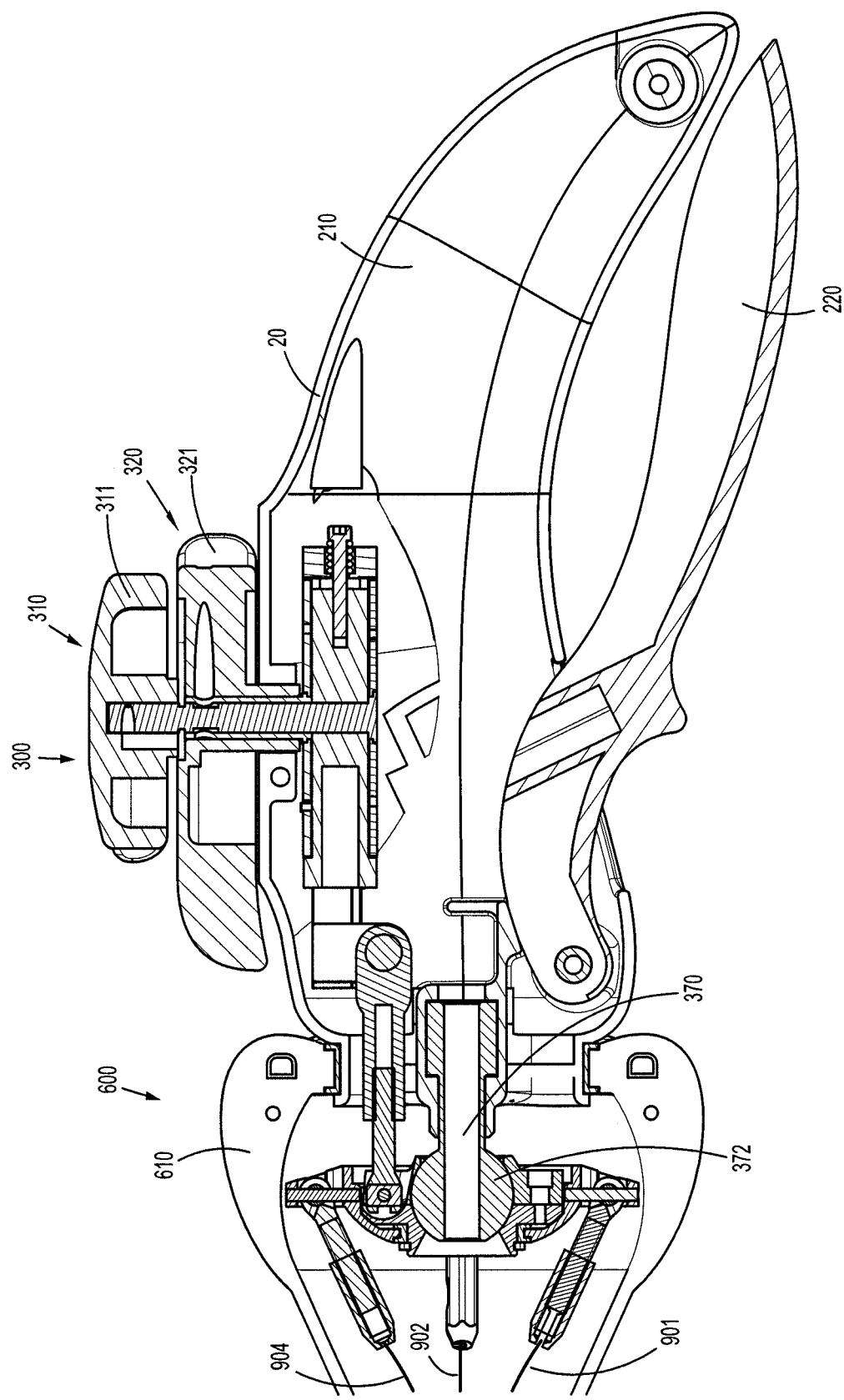
FIG. 2 is a cross-sectional view of the handle assembly, the articulation assembly and a portion of the rotation assembly taken along line 2-2 of FIG. 1.
Figure 3:
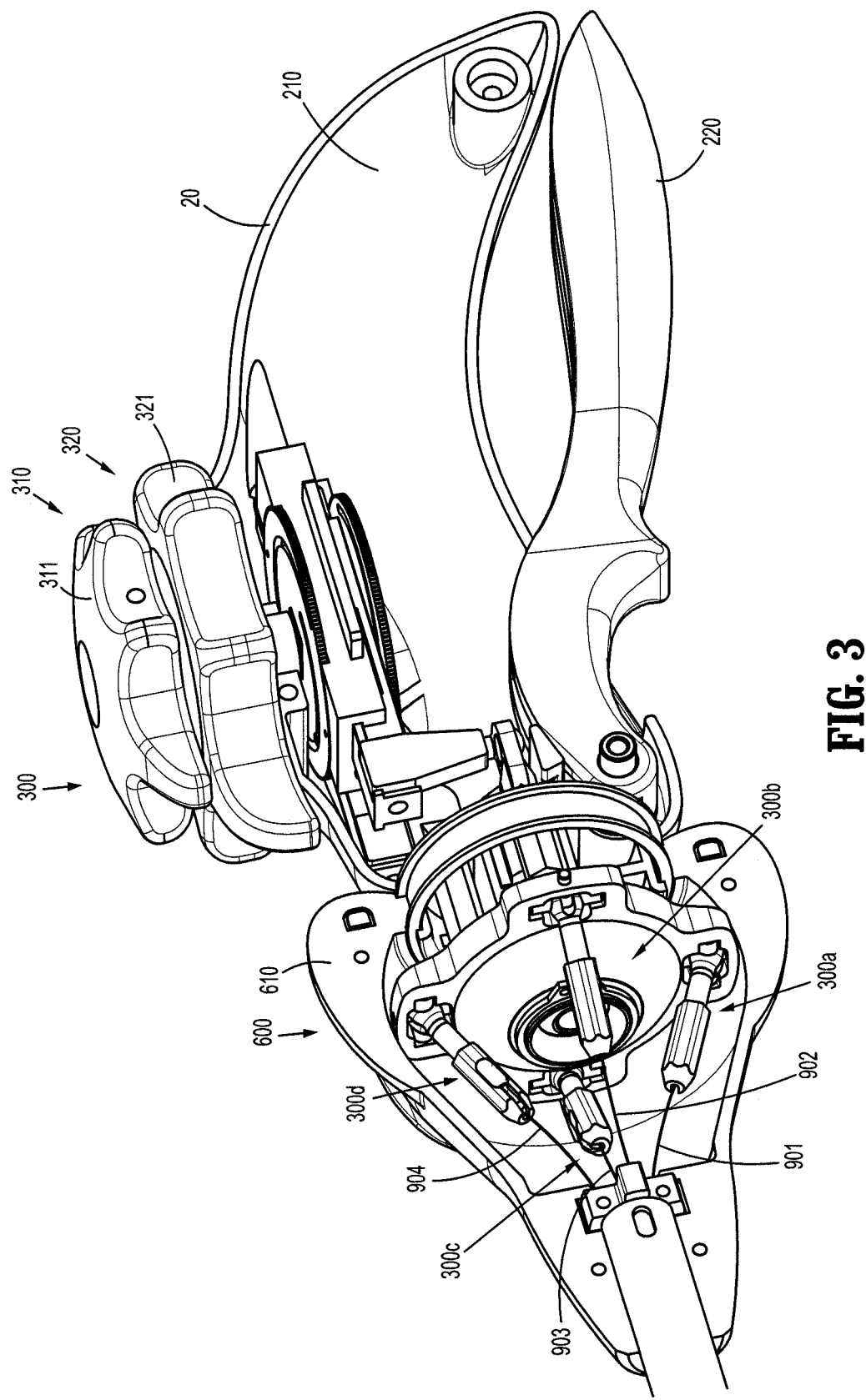
FIG. 3 is a partial perspective, partial cross-sectional view of the features shown in FIG. 2.

Referring initially to FIG. 1, one embodiment of an endoscopic vessel sealing forceps is depicted generally as 10. In the drawings and in the descriptions which follow, the term "proximal," as is traditional, will refer to the end of the forceps 10 which is closer to the user, while the term "distal" will refer to the end which is farther from the user. The forceps 10 comprises a housing 20, an end effector assembly 100 and an elongated shaft 12 extending therebetween to define a longitudinal axis A-A. A handle assembly 200, an articulation assembly 300 including two articulation controls 310 and 320, and a rotation assembly 600 are operable to control the end effector assembly 100 to grasp, seal and divide tubular vessels and vascular tissue. Although the forceps 10 is configured for use in connection with bipolar surgical procedures, various aspects of the present disclosure may also be employed for monopolar surgical procedures. Additionally, while the figures depict a certain type of a forceps, other types of forceps and other endoscopic surgical instruments are encompassed by the present disclosure. Further details of endoscopic forceps are described in commonly-owned U.S. Patent Publication No. 2010/0179540 to Marczyk et al., and U.S. patent application Ser. No. 12/718,143 to Marczyk et al., the entire contents of each of which are hereby incorporated by reference herein Further details of an endoscopic surgical stapling instrument including surgical fasteners are described in commonly-owned U.S. Pat. No. 6,953,139 to Milliman et al., the entire contents of which are hereby incorporated by reference herein.

Generally, handle assembly 200 includes a fixed handle 210 and a movable handle 220. The fixed handle 210 is integrally associated with the housing 20, and the movable handle 220 is movable relative to fixed handle 210 to induce relative movement between a pair of jaw members of the end effector assembly 100. The movable handle 220 is operatively coupled to the end effector assembly 100 via a drive rod or a flexible drive rod (not explicitly shown in the accompanying figures), which extends through the elongated shaft 12, and reciprocates to induce movement in the jaw members. The movable handle 220 may be approximated with fixed handle 210 to move the jaw members from an open position wherein the jaw members are disposed in spaced relation relative to one another, to a clamping or approximated position wherein the jaw members cooperate to grasp tissue therebetween. Electrosurgical energy may be transmitted through tissue grasped between jaw members to effect a tissue seal. Further details of these components and various other components of the disclosed forceps are disclosed in the references that have incorporated in detail above.

Elongated shaft 12 of forceps 10 includes a distal end 16 dimensioned to mechanically engage the end effector assembly 100 and a proximal end 14, which mechanically engages the housing 20. The elongated shaft 12 includes two portions: a proximal portion 12a defining a proximal shaft axis B-B and a distal portion 12b defining a distal shaft axis C-C.

The proximal portion 12a of the shaft 12 may exhibit various constructions. For example, the proximal portion 12a may be formed from a substantially rigid tube, from flexible tubing (e.g., plastic), or the proximal portion 12a may be formed as a composite of a flexible tube and a rigidizing element, such as a tube of braided steel, to provide axial (e.g., compressional) and rotational strength. In other embodiments, the proximal portion 12a may be constructed from a plastically deformable material.

Figure 16:
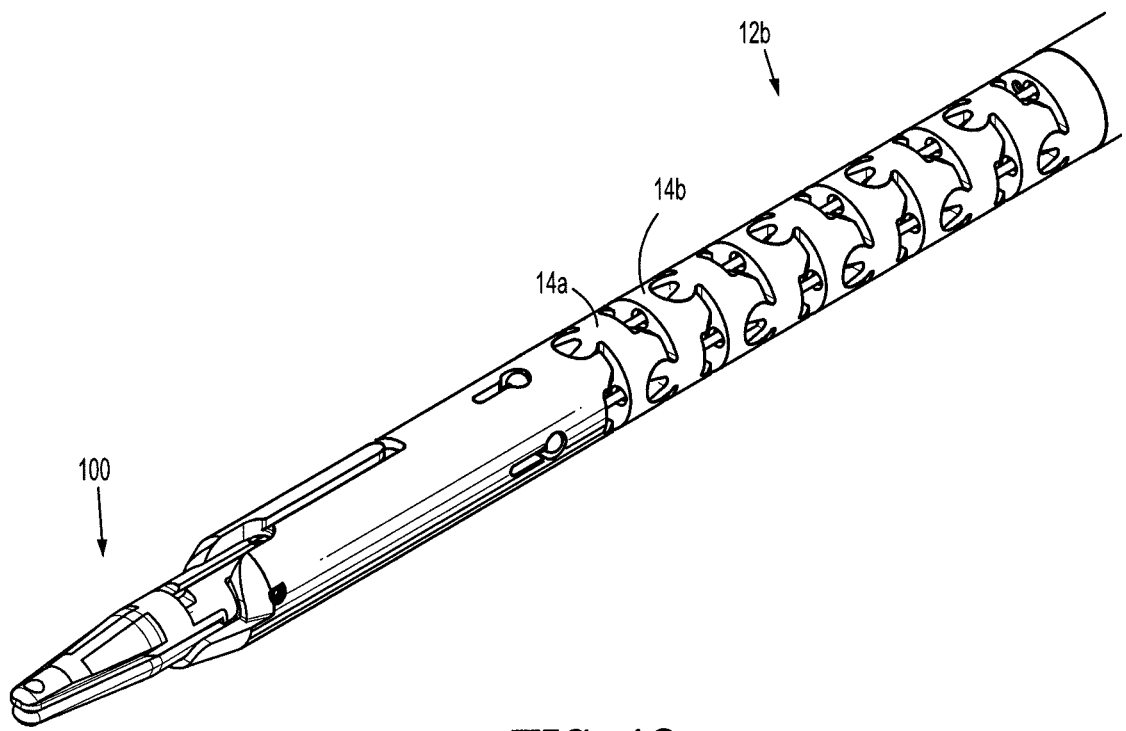
FIG. 16 is a perspective view of the area of detail illustrated in FIG. 1.

The distal portion 12b of shaft 12 includes an exterior casing or insulating material disposed over a plurality of links 14a, 14b, etc. (see FIGS. 16 and 24; hereinafter "links 14"). The links 14 are configured to pivot relative to one another to permit the distal portion 12b of the shaft 12 to articulate relative to the proximal shaft axis B-B. In one embodiment, the links 14 are nestingly engaged with one another to permit pivotal motion of the distal portion 12b in two orthogonal planes in response to movement of articulation controls 310 and 320. The links 14 may be shaped to permit the distal portion 12b of the shaft 12 to be self-centering, or to have a tendency to return to an unarticulated configuration.

Articulation assembly 300 sits atop housing 20 and is operable via articulation controls 310 and 320 to move the end effector assembly 100 (and the articulating distal portion 12b of the shaft 12) in the direction of arrows "U, D" and "R, L" relative to axis proximal shaft axis B-B as explained in more detail below.

Figure 4:
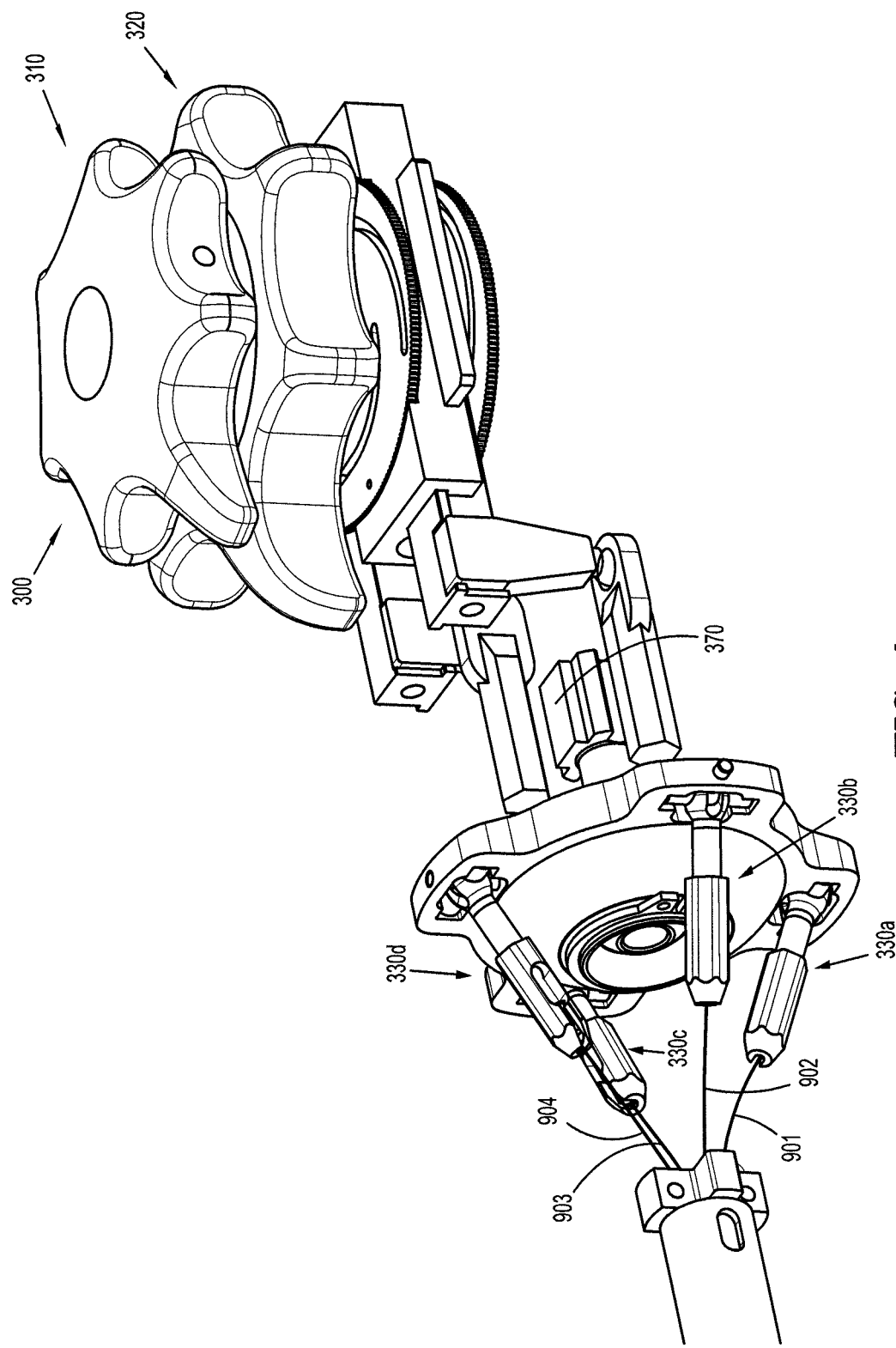
FIGS. 4 and 5 are perspective views of the articulation assembly of FIGS. 1-3.

The links 14 each include a central lumen extending longitudinally therethrough. The central lumen permits passage of various actuators, including a drive rod, a knife rod and four steering cables 901, 902, 903 and 904 (e.g., FIG. 4) through the elongated shaft 12.

The four steering cables 901-904 may be substantially elastic and slideably extend through elongated shaft 12. A distal end of the each of the steering cables 901-904 is mechanically engaged with the end effector 100. Proximal ends of the steering cables 901-904 are operatively coupled to the articulation controls 310, 320 as described below.

Referring now to FIGS. 2-6 the articulation assembly 300 permits selective articulation of the end effector assembly 100 to facilitate the manipulation and grasping of tissue. More particularly, the two controls 310 and 320 include selectively rotatable wheels, 311 and 321, respectively, that sit atop the housing 20. Each wheel, e.g., wheel 311, is independently moveable relative to the other wheel, e.g., 321, and allows a user to selectively articulate the end effector assembly 100 in a given plane of articulation relative to the longitudinal axis A-A. For example, rotation of wheel 311 articulates the end effector assembly 100 along arrows R, L (or right-to-left articulation) by inducing a differential tension and a corresponding motion in steering cables 902 and 903. Similarly, rotation of wheel 321 articulates the end effector assembly along arrows U, D (or up-and-down articulation) by inducing a differential tension and a corresponding motion in steering cables 901 and 904.

The articulation assembly 300 and the rotation assembly 600, comprise the articulating-rotating mechanism and include wheels 311 and 321, and a rotation knob 610 to effect articulation and/or rotation of the end effector 100. Details regarding the various components of the articulating-rotating mechanism are described in detail below.

Distal ends of cables 901-904 are disposed in mechanical engagement with end effector 100, and travel proximally through shaft 12, as described above. Proximal ends of cables 901-904 are disposed in mechanical cooperation with post assemblies 330a-300d, respectively. Each post assembly 330 includes a sleeve 332, which is disposed at least partially around a post 334 (see FIGS. 9 and 10). It is envisioned that the sleeves 332 and the posts 334 are threadably engaged with each other to allow the tension of the cables to be adjusted.

Figure 6:
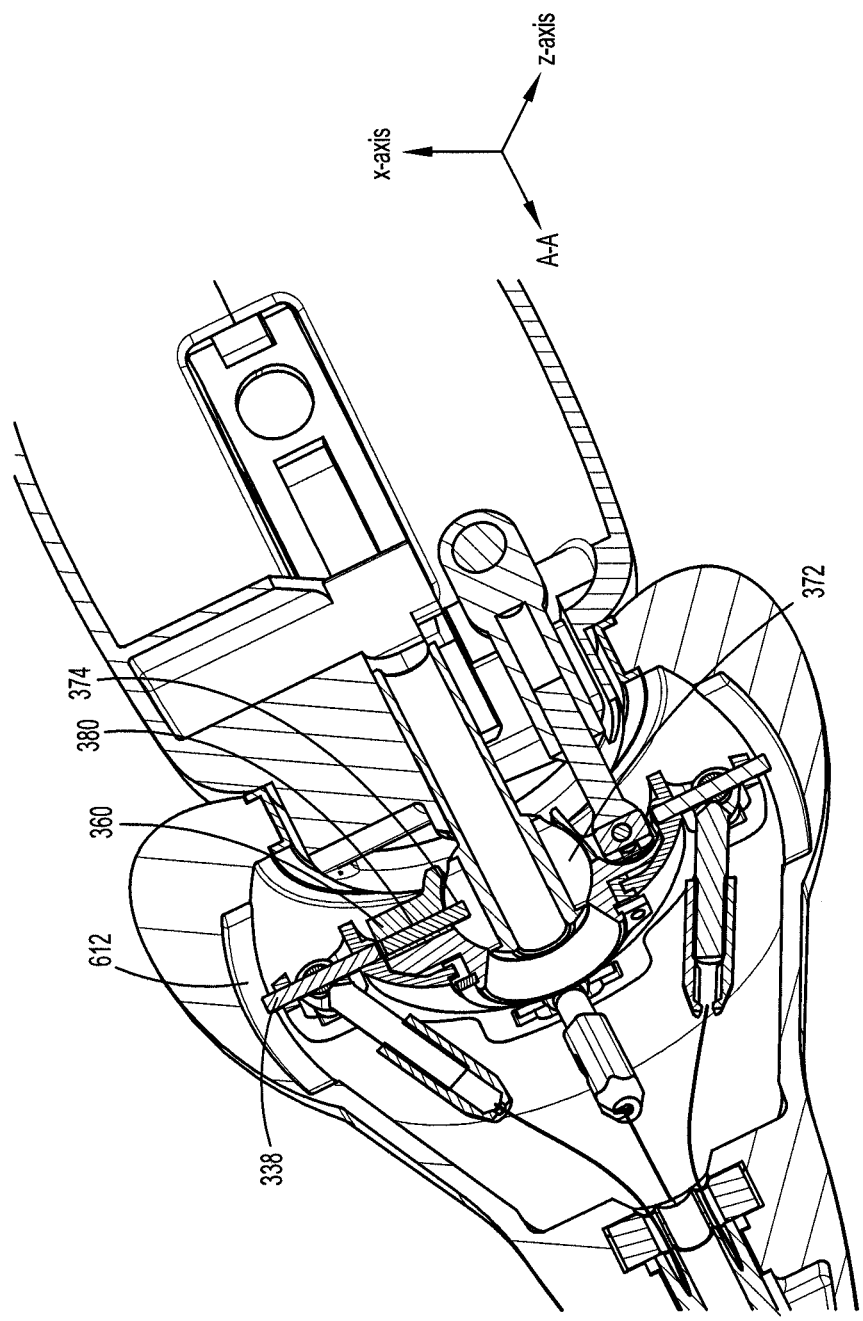
FIG. 6 is a perspective view of a portion of the articulation assembly and a portion of the rotation assembly taken along line 6-6 of FIG. 1.
Figure 7:
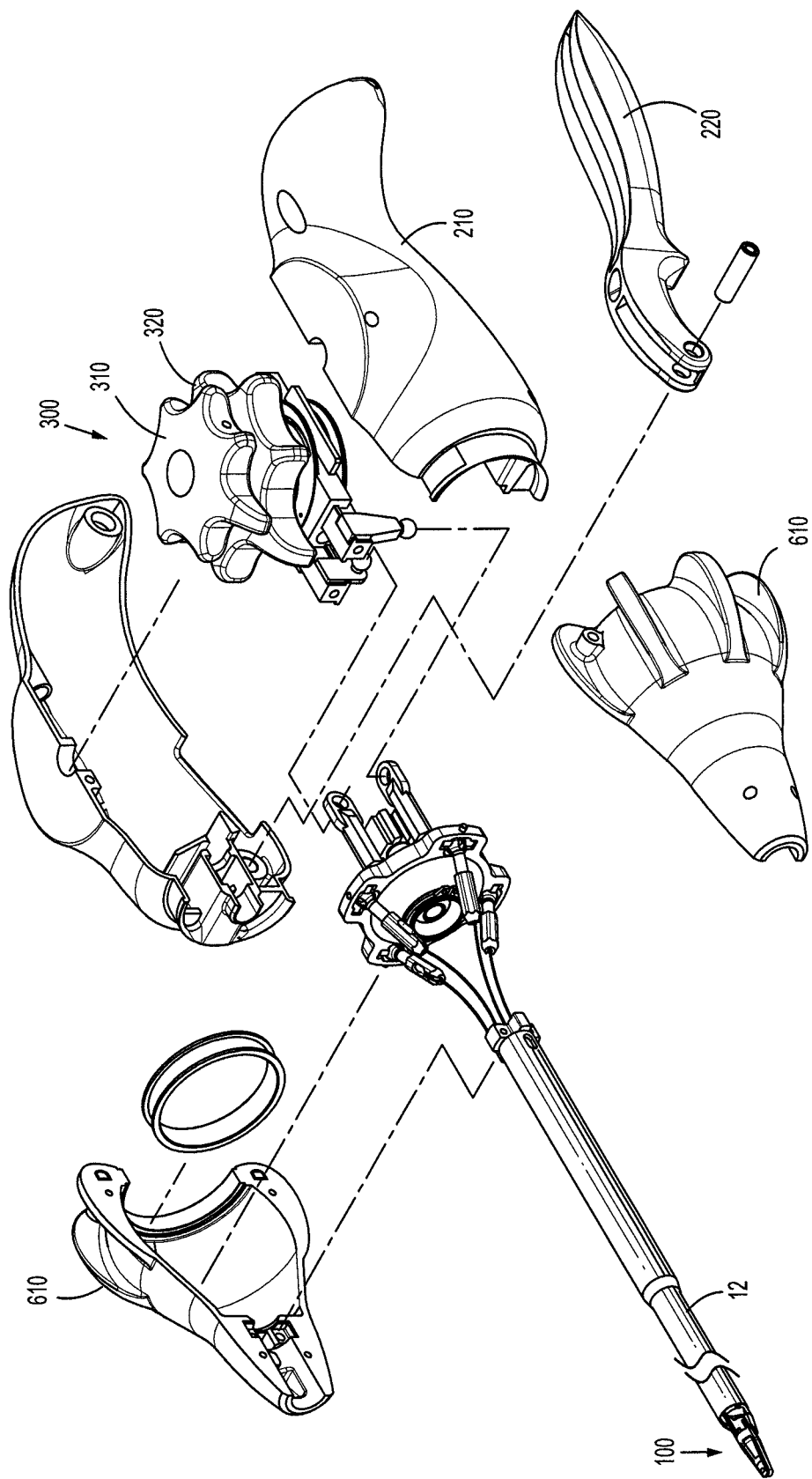
FIG. 7 is an assembly view of the forceps of FIG. 1.
Figure 8:
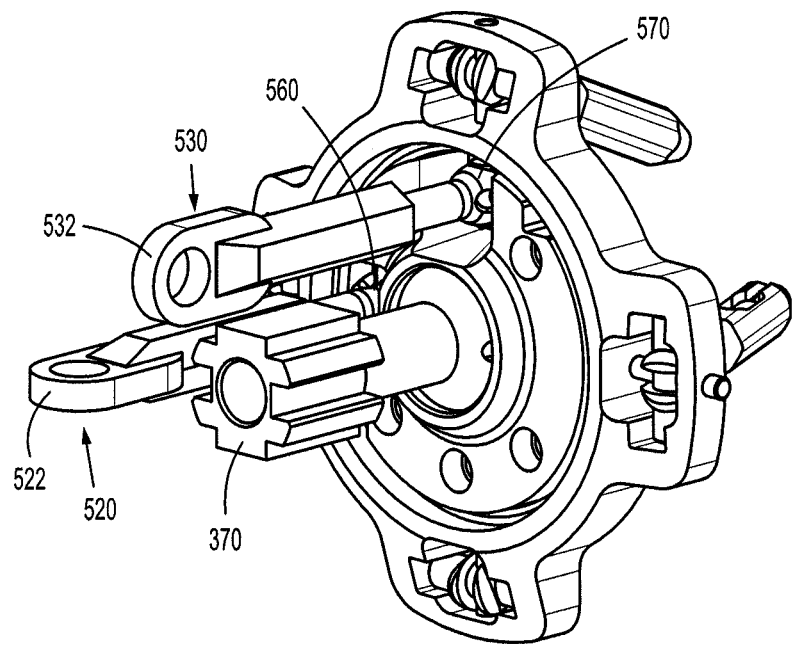
FIGS. 8 and 9 are perspective views of a portion of the articulation assembly of the present disclosure.
Figure 9:
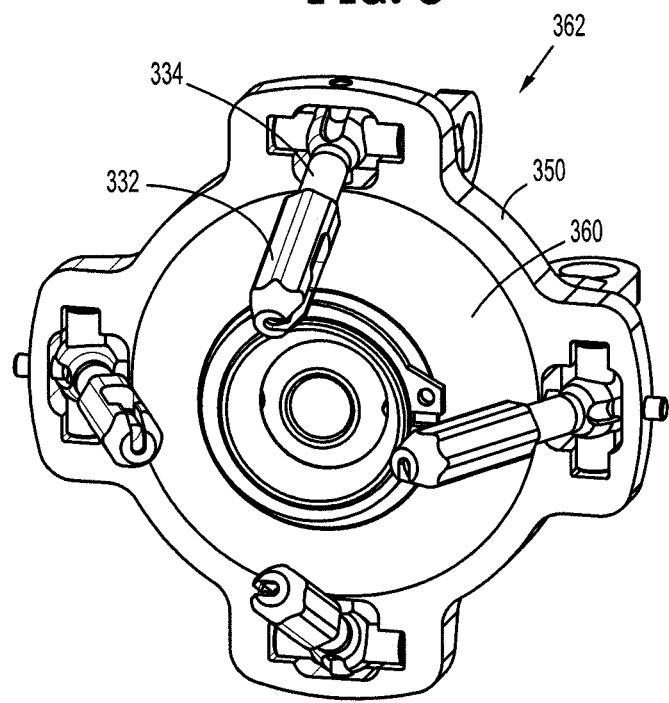
Figure 10:
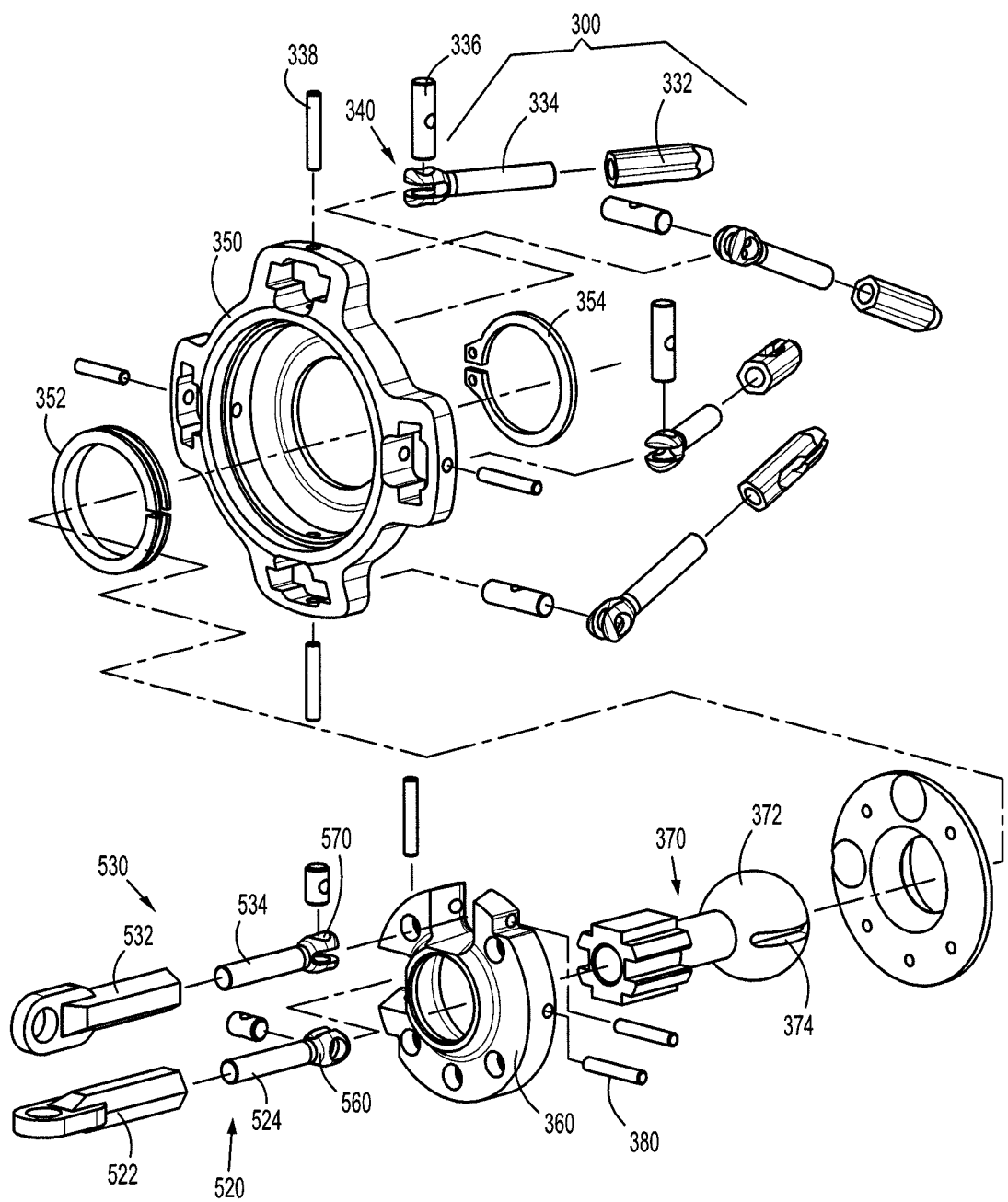
FIG. 10 is an assembly view of the portion of the articulation assembly of FIGS. 8 and 9.
Figure 11:
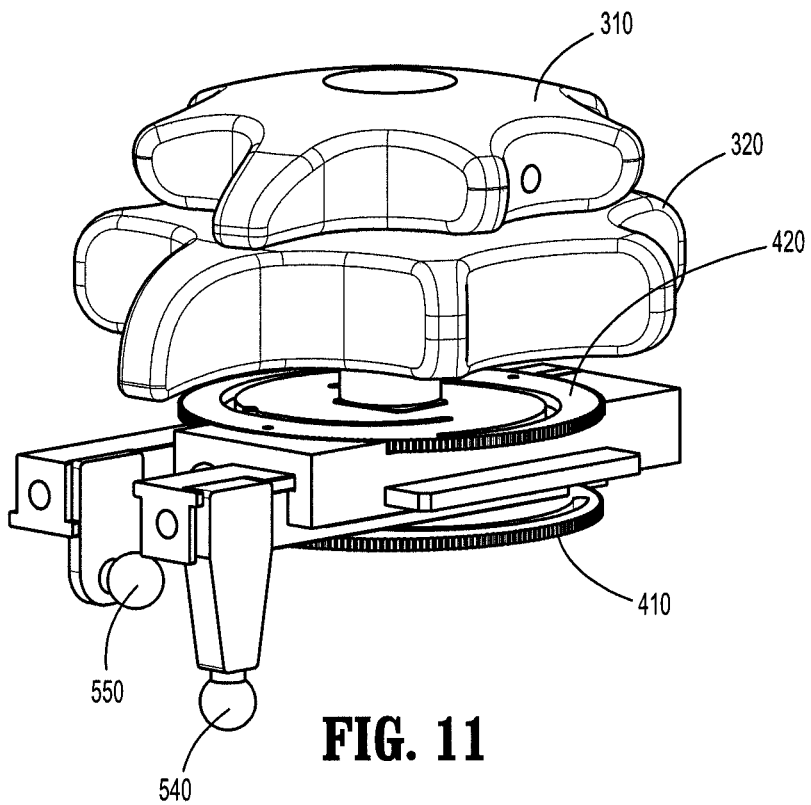
FIGS. 11-14 are perspective views of another portion of the articulation assembly.
Figure 12:
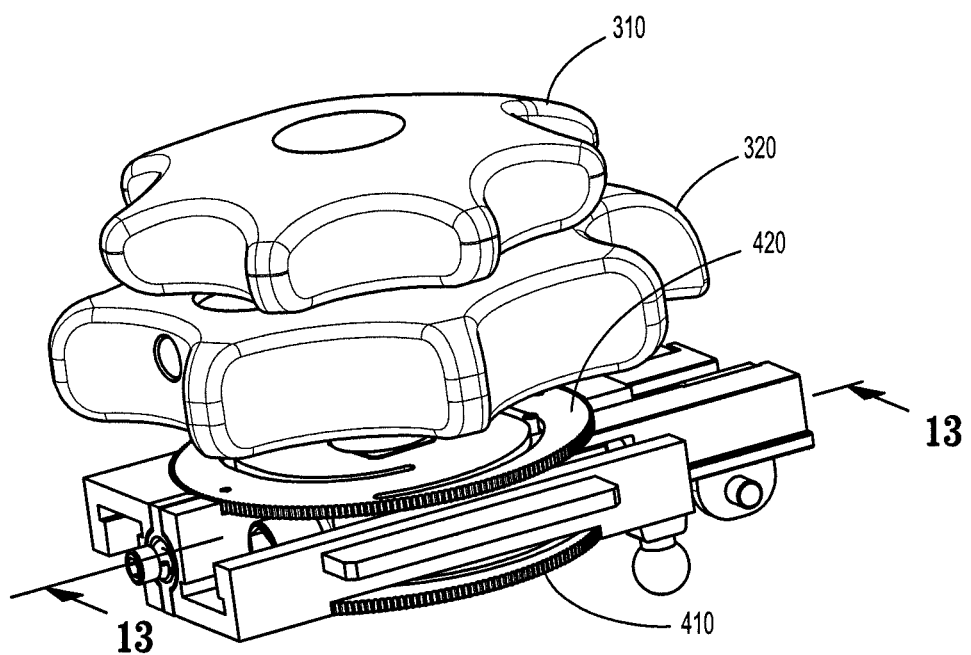
Figure 13:
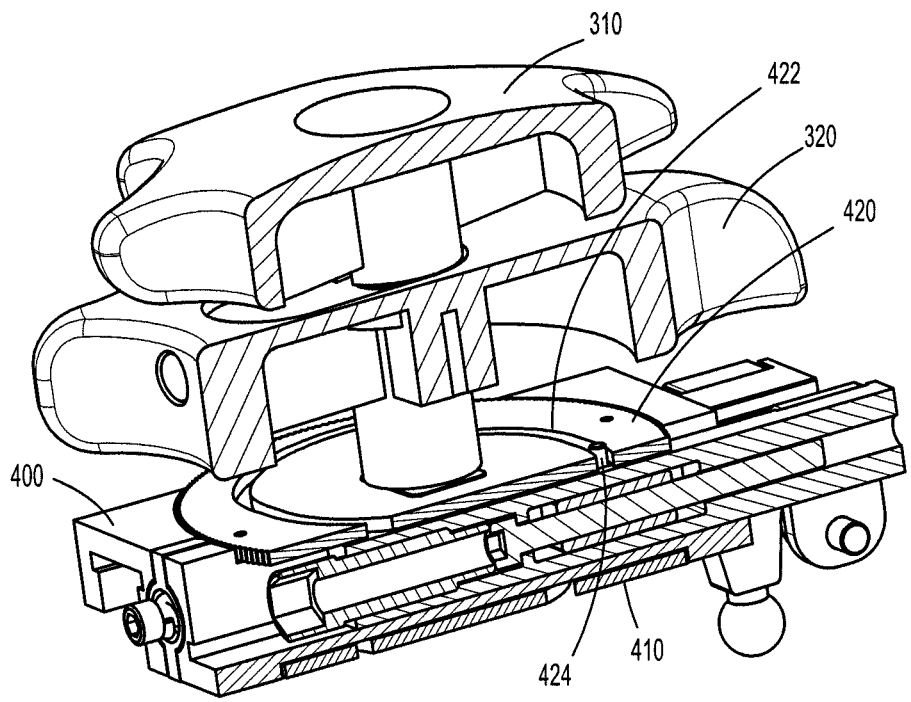
Figure 14:
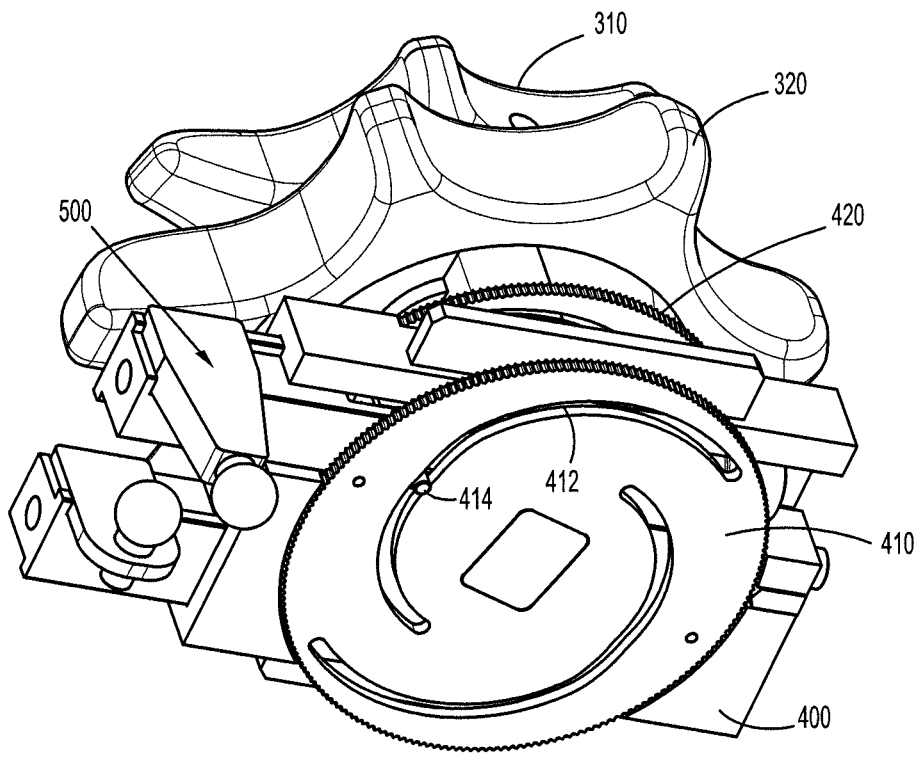

With particular reference to FIGS. 9 and 10, an outer disc 350 and an inner disc 360 comprise a disc assembly 362. Each post 334 is connected to outer disc 350 via pins 336, 338 and a ball joint 340. The interaction between the posts 334 and the outer disc 350 allow the posts 334 to swivel about pins 336, 338 with respect to outer disc 350. Outer disc 350 radially surrounds inner disc 360 and is rotatable around inner disc 360. That is, a series of bearings 352 and clips 354 are disposed between inner disc 360 and outer disc 350 to enable outer disc 350 to rotate with respect to inner disc 360. Additionally, as shown in FIG. 6, an outer portion of pins 338 engages a groove 612 in rotation knob 610. Thus, as rotation knob 610 rotates, outer disc 350, post assemblies 330, and cables 901-904 also rotate, which causes end effector 100 to rotate around longitudinal axis A-A (or around the w-axis as discussed below with reference to FIG. 24).

The inner disc 360 is connected to housing 20 via a connector 370. More particularly, inner disc 360 is connected to a distal portion of connector 370 via a ball-joint connection 372, and connector 370 is stationary with respect to housing 20. Additionally, connector 370 is hollow, such that portions of elongated mechanisms (e.g., firing rod, knife rod, etc.) can be advanced between housing 20 and shaft 12. Such elongated mechanisms are not illustrated in the accompanying figures in the interest of visual clarity.

A pin 380 engages both ball-joint connection 372 and inner disc 360. An outer portion of pin 380 engages inner disc 360, and an inner portion of pin 380 engages a slot 374 within ball-joint connection 372 (see FIG. 6). This connection results in inner disc 360 being able to rotate with respect to the X- and Z-axes, but unable to rotate with respect to the longitudinal axis A-A. The orientation of inner disc 360 and outer disc 350 results in outer disc 350 rotating with inner disc 360 around the X- and Z-axes. Additionally, as discussed above, outer disc 350 is also able to rotate around the longitudinal axis A-A when driven by rotation knob 610.

Figure 17:
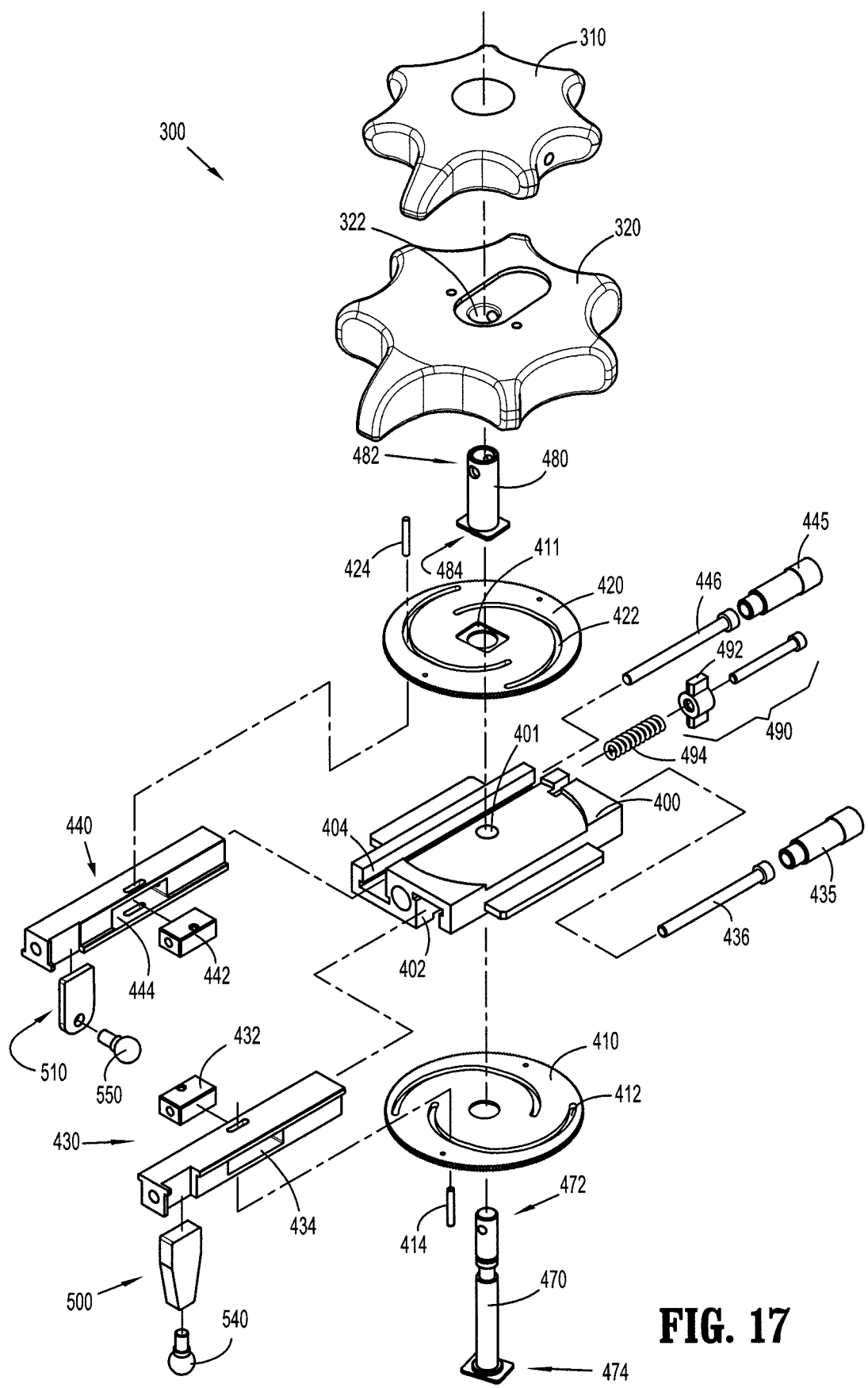
FIG. 17 is an assembly view of a portion of the articulation assembly of the present disclosure.
Figure 18:
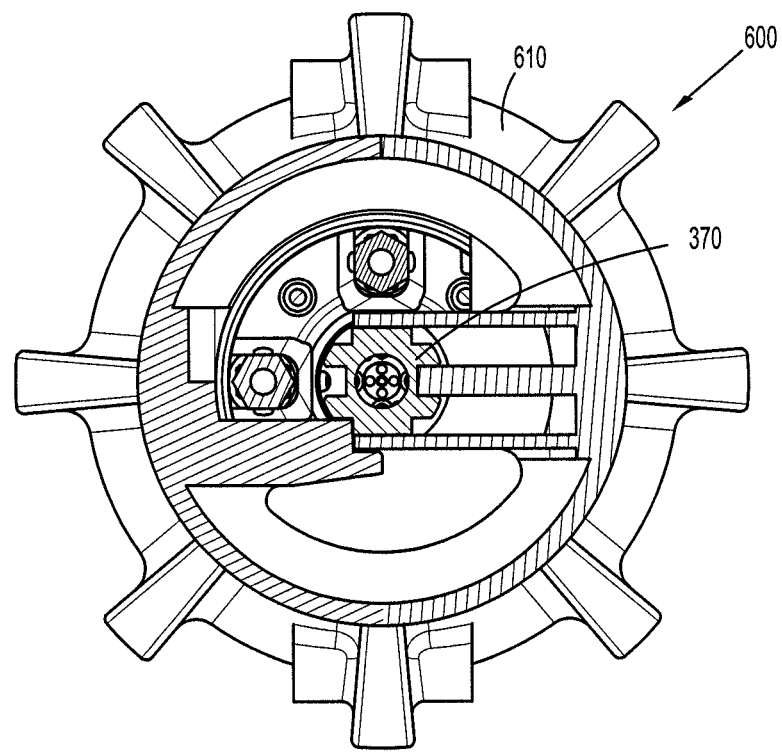
FIGS. 18-20 are cross-sectional views of portions of the articulation assembly and the rotation assembly of the present disclosure.
Figure 19:
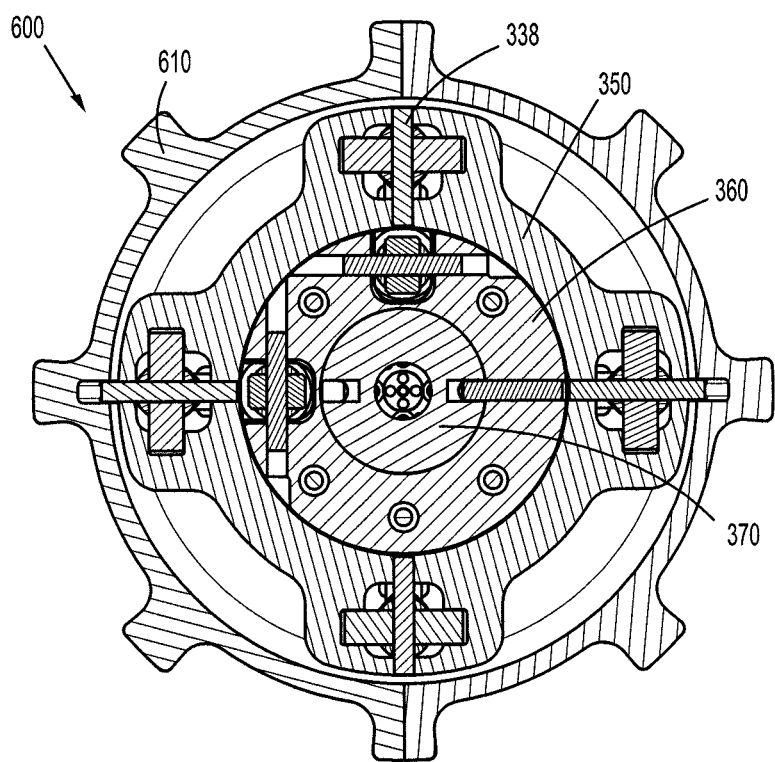
Figure 20:
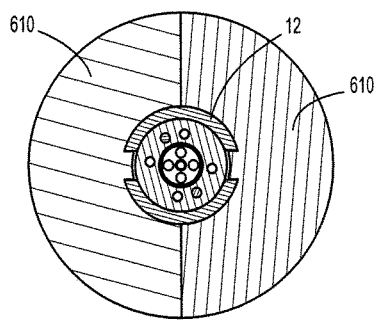
Figure 21:
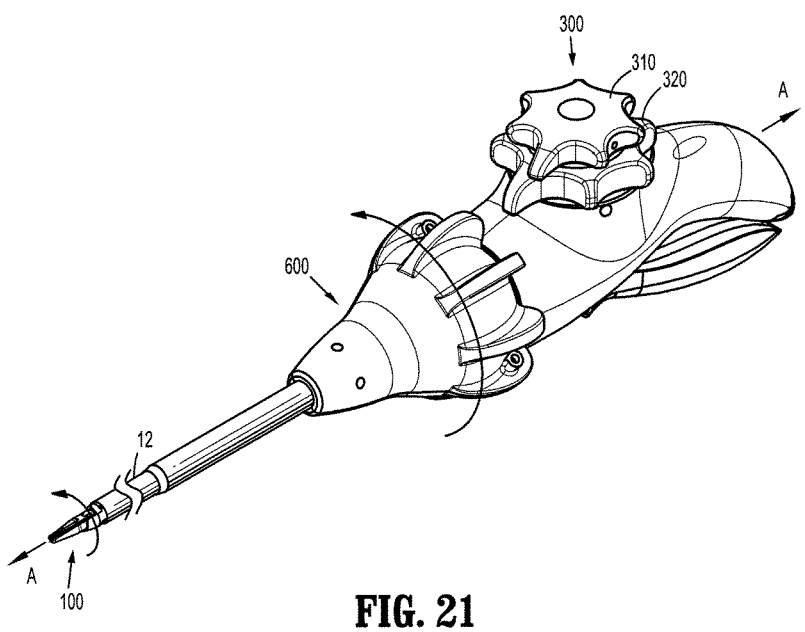
FIG. 21 is a perspective view of the forceps of the present disclosure.
Figure 22:
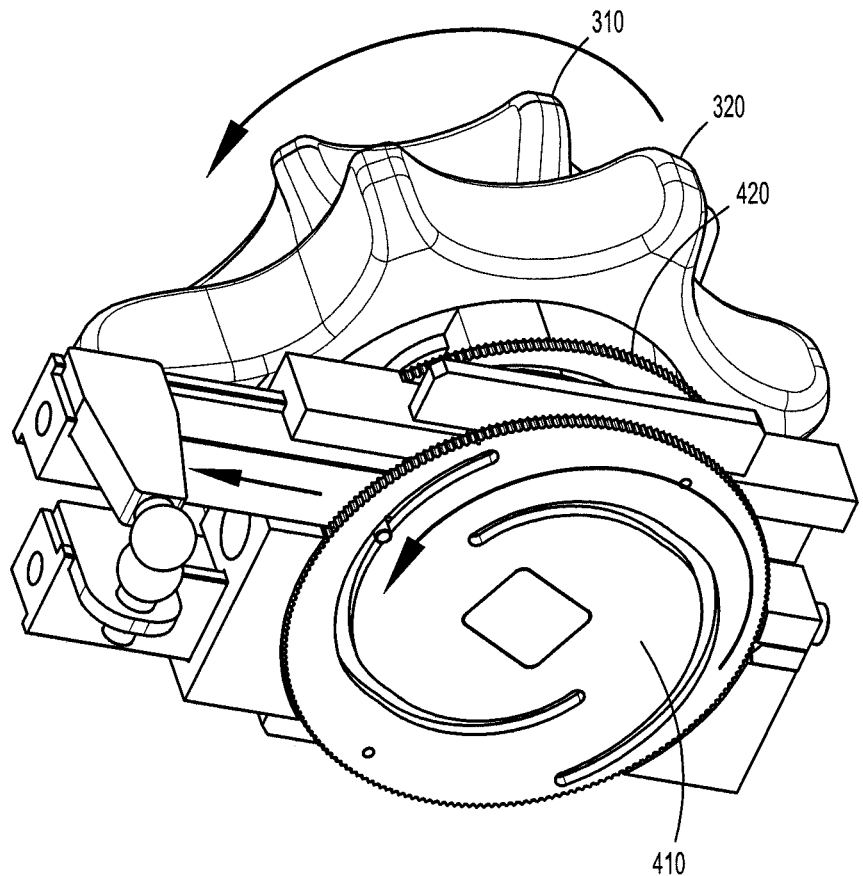
FIGS. 22 and 23 are views of a portion of the articulation assembly of the present disclosure.

Referring now to FIG. 17, for example, articulation assembly 300 also includes a block 400, a first disc 410, a second disc 420, a first slider 430, and a second slider 440. First articulation control 310 is connected to first disc 410 via a first post 470; second articulation control 320 is connected to second disc 420 via a second post 480. More particularly, an upper portion 472 of first post 470 is mechanically coupled to first articulation control 310 (e.g., via a pin), and a lower portion 474 of first post 470 is mechanically coupled to first disc 410. An upper portion 482 of second post 480 is mechanically coupled to second articulation control 320 (e.g., via a pin), and a lower portion 484 of second post 480 is mechanically coupled to second disc 420. As shown in FIG. 17, lower portions 474, 484 of posts 470, 480 may include a polygonal-shape (e.g. a square) that is dimensioned to fit within a corresponding recess 411 in the corresponding disc 410, 420 (the lower portion of first disc 410 is not shown). Additionally, an outer diameter of first post 470 is smaller than an inner diameter of second post 480, thus enabling first post 470 to extend through second post 480. First post 470 also extends through an opening 401 in block 400 and an opening 322 in first disc 320. As such, rotation of first articulation control 310 causes rotation of first disc 410, and rotation of second articulation control 320 causes rotation of second disc 420.

Figure 15:
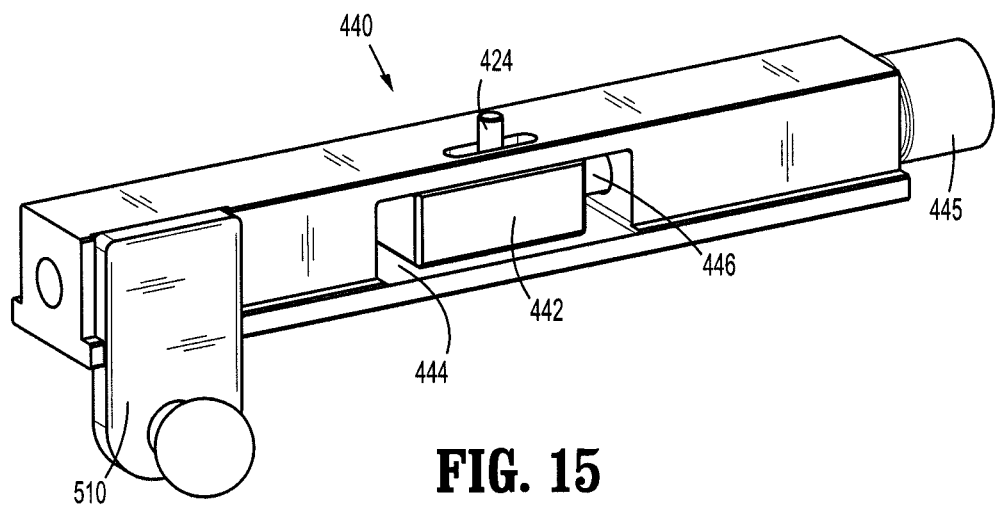
FIG. 15 is a perspective view of a slider of the articulation mechanism of the present disclosure.

Each disc 410, 420 has at least one arcuate slot 412, 422 therein. In the illustrated embodiments, discs 410, 420 each include two slots. In this embodiment, discs 410, 420 are identical to each other (and flipped about the Z-axis (FIG. 6) with respect to each other), e.g., to facilitate manufacturing. Following pins 414, 424 extend through respective slots 412, 422, and are coupled to respective sliders 430, 440. The location of following pins 414, 424 can be adjusted within respective sliders 430, 440 by the mechanisms illustrated in FIGS. 15 and 17. More particularly, sliders 430, 440 each include a slidable block 432, 442 connected to respective pins 414, 424, and which are slidable within a cavity 434, 444. Proximal screws 435, 445 threadably engage sliders 430, 440, and each abut a respective distal screw 436, 446. Distal screws 436, 446 extend through and threadably engage respective slidable blocks 432, 442, such that rotation of proximal screws 435, 445 causes translation of respective slidable blocks 432, 442, and thus pins 414, 424.

Additionally, sliders 430, 440 slidingly engage longitudinal slots 402, 404, respectively, in block 400. As such, rotation of articulation control 310 causes rotation of first disc 410, which causes following pin 414 to move along arcuate slot 412, which causes slider 430 to move longitudinally through longitudinal slot 402 in block 400. Likewise, rotation of articulation control 320 causes longitudinal translation of slider 440 with respect to block 400.

Figure 5:
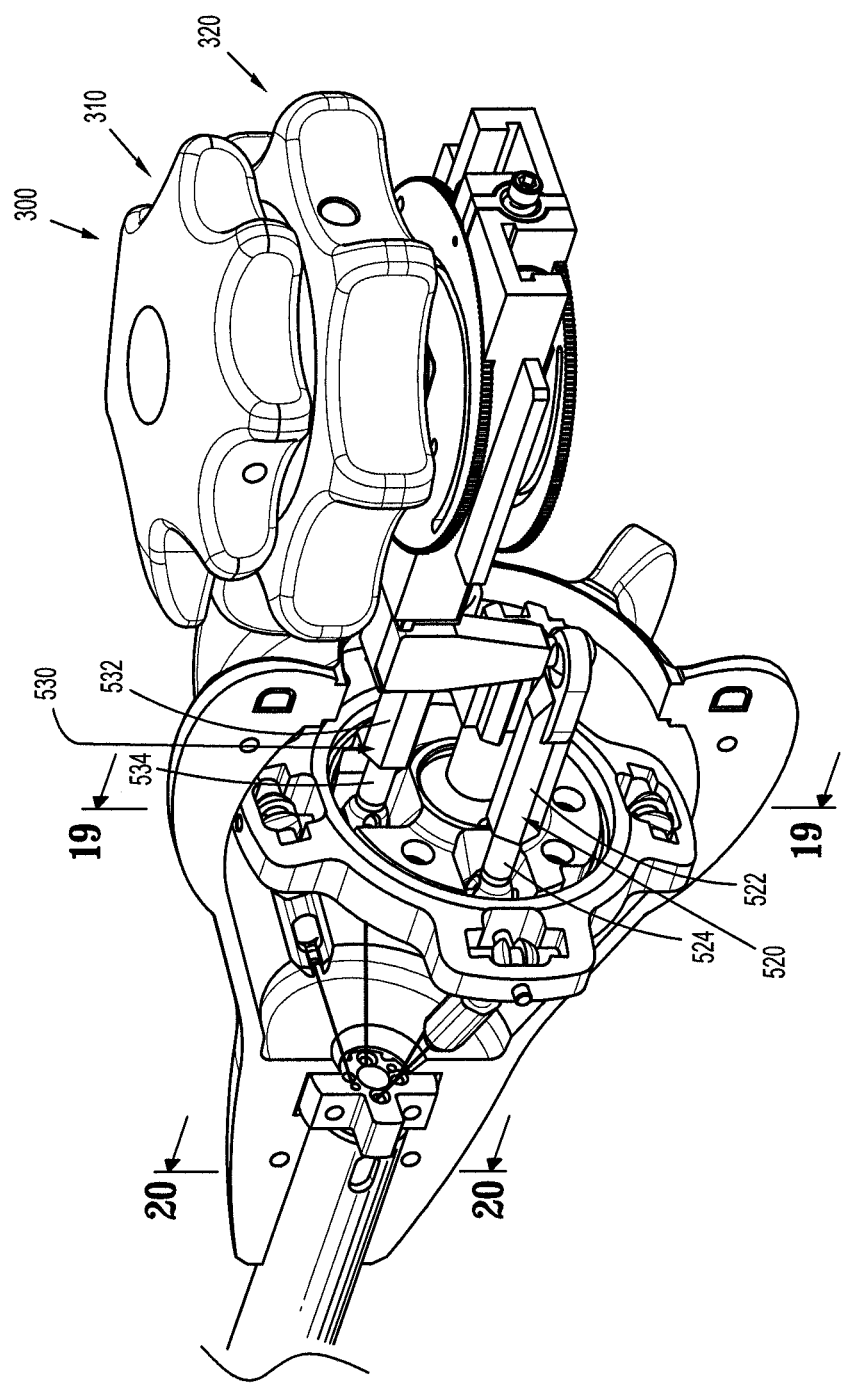

Sliders 430, 440 are connected to inner disc 360 via a first connecting arms 500, 510 and second connecting arms 520, 530. First connecting arms 500, 510 downwardly depend from respective sliders 430, 440 and are connected to second connecting arms 520, 530, respectively, via ball joints 540, 550. Second connecting arms 520, 530 include proximal portions 522, 532 and distal portions 524, 534, which are longitudinally translatable (e.g., threaded) with respect to one another to allow the length of second connecting arms 520, 530 to be adjusted. Second connecting arms 520, 530 are connected to inner disc 360 via ball joints 560, 570. The ball joint 560, 570 connections allow three-dimensional movement (i.e., about the longitudinal axis A-A and the Y- and Z-axes) of disc assembly 362. Additionally, as shown in FIG. 5, for example, first connecting arm 520 is radially offset 90° from second connecting arm 530. That is, in the illustrated embodiment, first connecting arm 520 engages inner disc 360 at a top portion thereof (i.e., in a 12:00 position in FIG. 5), and second connecting arm 530 engages inner disc 360 at a lateral portion thereof (i.e., in a 9:00 position in FIG. 5).

Figure 23:
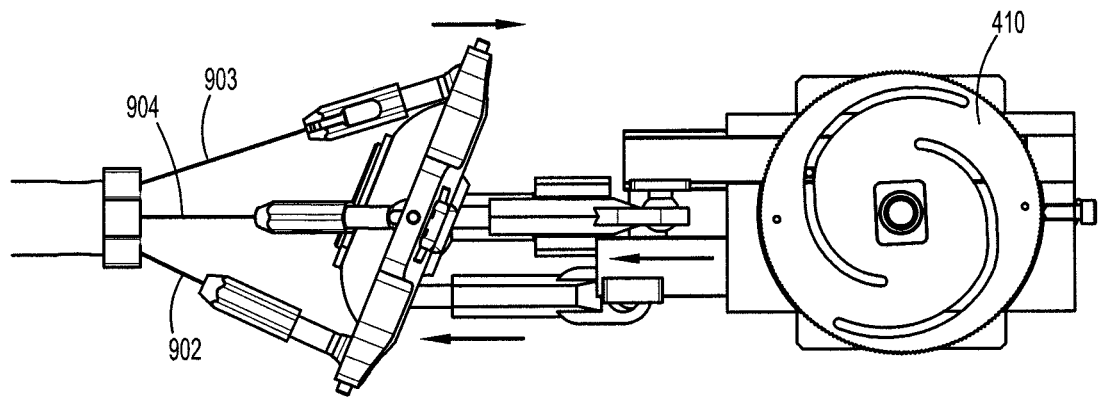

In use, rotation of first articulation control 310 causes first slider 430 to longitudinally translate, which causes a top portion of disc assembly 362 to move distally/proximally. Such movement by the top portion of disc assembly 362 causes upper cable 904 and lower cable 901 to in opposite directions from one another (i.e., one cable moves distally, the other cable moves proximally). When upper cable 904 is moved distally (i.e., produces slack) and lower cable 901 is moved proximally (i.e., produces tension), end effector 100 articulates downwardly, in the substantial direction of arrow "D" in FIG. 1. When upper cable 904 is moved proximally and lower cable 901 is moved distally, end effector 100 articulates upwardly, in the substantial direction of arrow "U" in FIG. 1. As can be appreciated, rotation of second articulation control 302 causes translation of cables 902, 903 (see FIG. 23), which causes end effector 100 to articulate in the directions of arrows "R" and "L" in FIG. 1.

Figure 24:
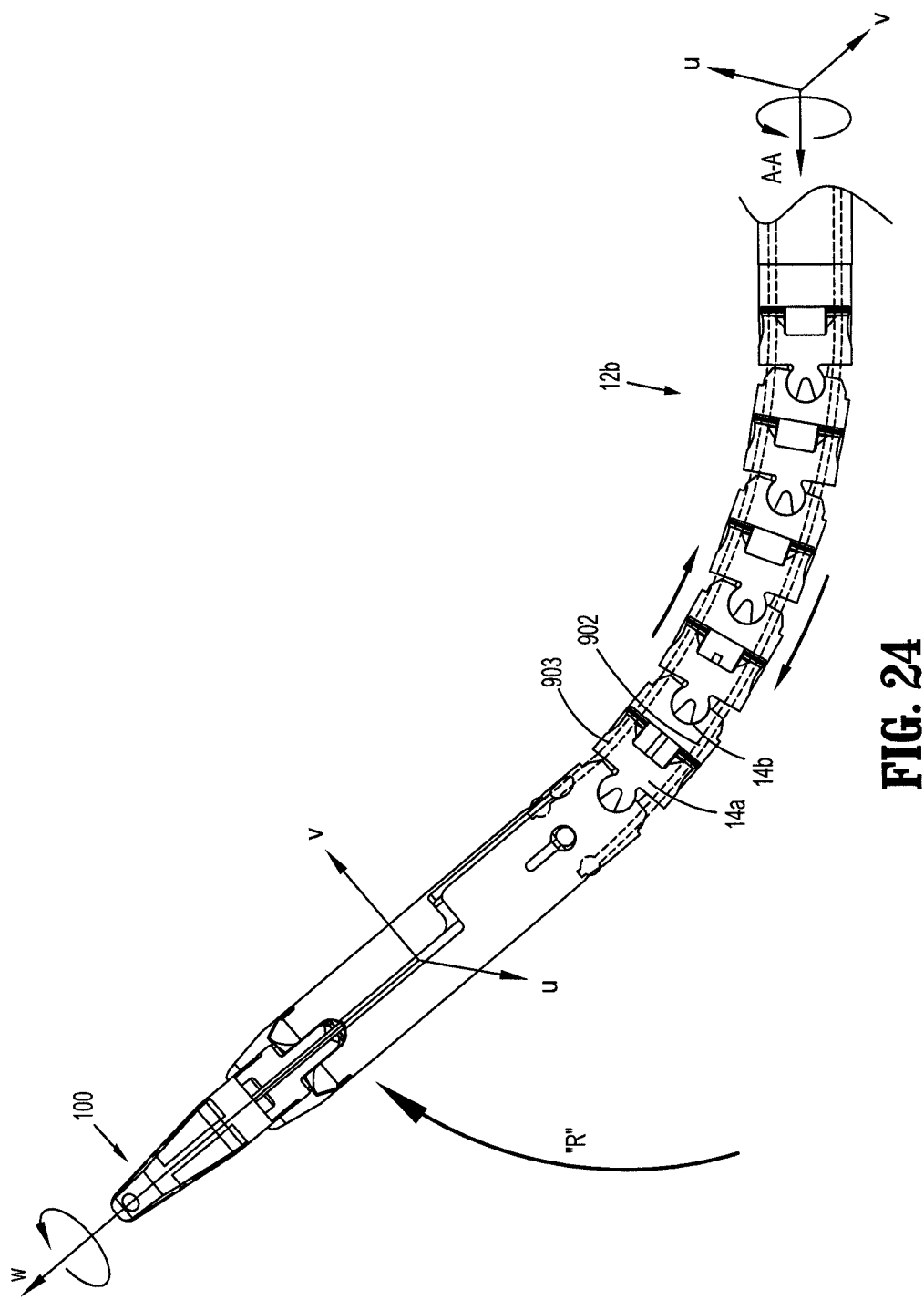
FIG. 24 illustrates an articulated distal end of the forceps of the present disclosure.

Further, with particular reference to FIG. 24, when the end effector 100 is articulated in a particular direction and amount (e.g., "R" in FIG. 24), and when coordinate system {u, v, w} is associated with the end effector 100. FIG. 24 illustrates that rotation of rotation knob 610 about longitudinal axis A-A, causes the end effector 100 to rotate about axis "w"; end effector 100 does not rotate around longitudinal axis A-A. Thus, the end effector 100 maintains its articulation (i.e., its "R" position in FIG. 24) while being able to rotate about the w-axis.

Additionally, in the illustrated embodiments, first disc 410 and second disc 420 include serrations along perimeters thereof. A member 490, as shown in FIG. 17, includes a distal end 492 that is biased into each disc 410, 420 via a spring 494, such that rotation of articulation control 310 and/or 320 causes distal end 492 of member 490 to contact successive serrations, which produces an audible sound to facilitate use.

Figure 25:
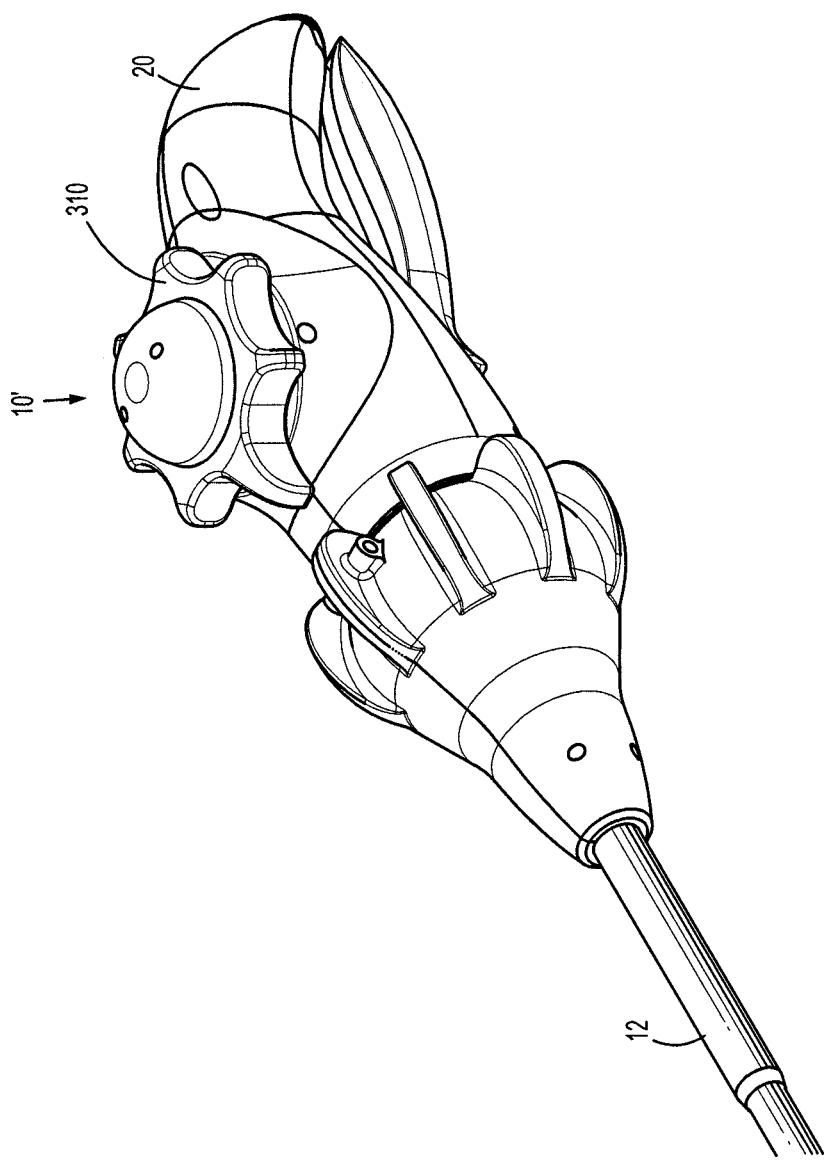
FIG. 25 is a perspective view of a handle portion of a second embodiment of the disclosed forceps.
Figure 26:
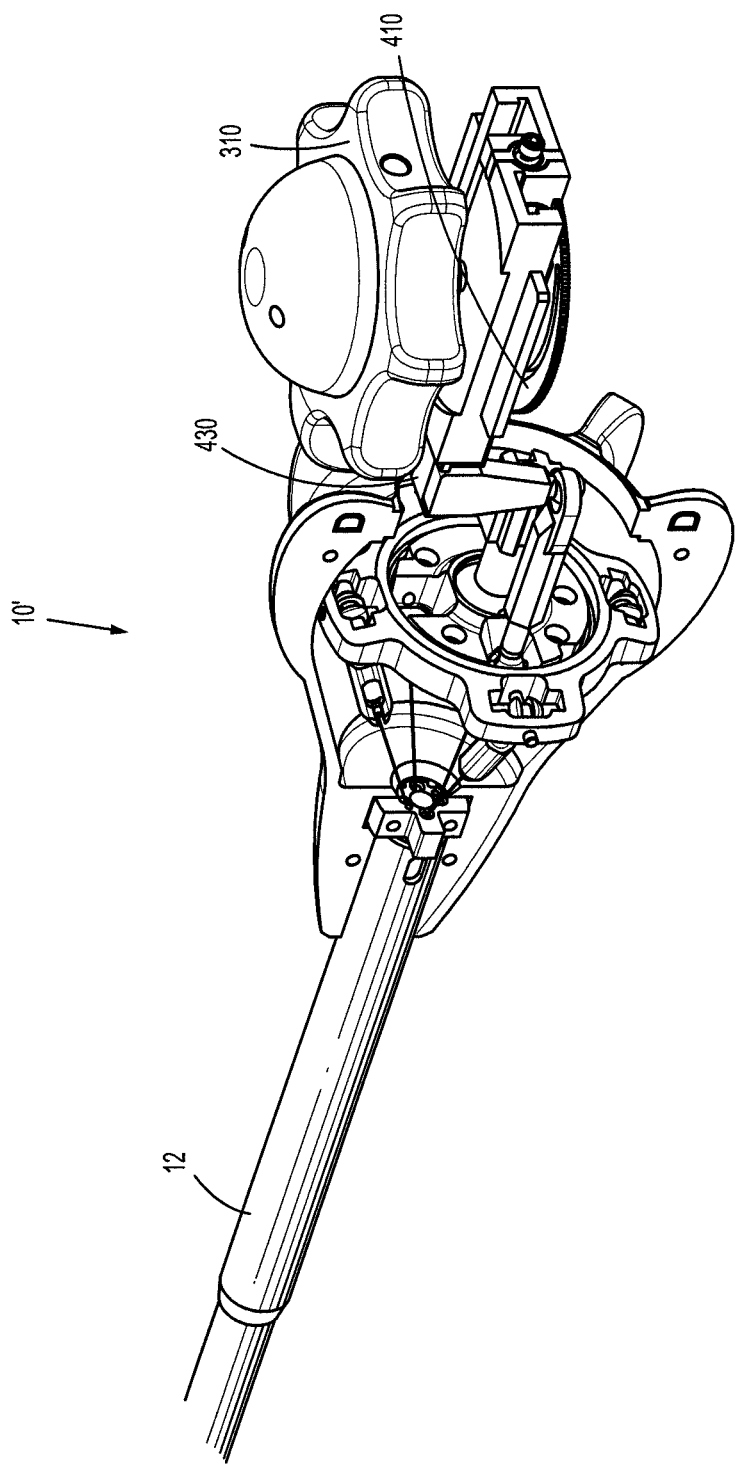
FIG. 26 is a perspective view of the handle portion of FIG. 25 with portions of the handle assembly removed.

Another forceps 10' according to an embodiment of the present disclosure is illustrated in FIGS. 25 and 26. This embodiment includes a single articulation control 310, a single disc 410, and a single slider 430. In this embodiment, a user can rotate articulation control 310 in addition to the housing 20 for full articulation control of end effector 100.

FIGS. 27 and 28 illustrate another embodiment of a forceps 10″ having housing 20′, which is usable with the articulation assembly 300 and rotation assembly 600 of the present disclosure. As illustrated, housing 20′ lacks a movable handle. Here, it is envisioned that any type of actuation mechanism, including powered actuation, is usable with forceps 10″.

While several embodiments of the disclosure have been depicted in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument comprising:
    a handle assembly;
    an elongated shaft extending distally from the handle assembly and defining a first longitudinal axis;
    an end effector disposed in mechanical cooperation with a distal portion of the elongated shaft, the end effector defining a second longitudinal axis and including a pair of jaw members;
    a rotation mechanism disposed in mechanical cooperation with the handle assembly and configured to rotate the pair of jaw members of the end effector about the second longitudinal axis by a rotation of at least a portion of the rotation mechanism about the first longitudinal axis relative to the handle assembly;
    an articulation mechanism disposed in mechanical cooperation with the handle assembly and configured to move the end effector from a first position where the first longitudinal axis is aligned with the second longitudinal axis to a second position where the second longitudinal axis is displaced from the first longitudinal axis, the articulation mechanism including:
        a first articulation control disposed in mechanical cooperation with the handle assembly;
        a second articulation control disposed in mechanical cooperation with the handle assembly, the first articulation control and the second articulation control are independently actuatable with respect to each other;
        a first cable, a distal portion of the first cable disposed in mechanical cooperation with the end effector;
        a second cable, a distal portion of the second cable disposed in mechanical cooperation with the end effector;
        a third cable, a distal portion of the third cable disposed in mechanical cooperation with the end effector; and
        a fourth cable, a distal portion of the fourth cable disposed in mechanical cooperation with the end effector;
        wherein the first articulation control is actuatable in a first direction to cause the first cable to move distally with respect to the handle assembly and to cause the second cable to move proximally with respect to the handle assembly, and wherein the second articulation control is actuatable in a second direction to cause the third cable to move distally with respect to the handle assembly and to cause the fourth cable to move proximally with respect to the handle assembly;
        a first disc;
        a second disc; and
        a link mechanism,
        wherein proximal portions of the first cable, the second cable, the third cable and the fourth cable are coupled to the first disc, the first disc is rotatable about the first longitudinal axis relative to the handle assembly, and the link mechanism connects the first articulation control and the second articulation control to the second disc.

2. The surgical instrument according to claim 1, wherein the rotation mechanism is configured to rotate the elongated shaft about the first longitudinal axis and relative to the handle assembly.

3. The surgical instrument according to claim 1, wherein the rotation mechanism is configured to rotate the first cable and the second cable about the first longitudinal axis.

4. The surgical instrument according to claim 1, wherein the articulation mechanism further includes a first slider, the second disc disposed in mechanical cooperation with the first articulation control and the first slider disposed in mechanical cooperation with the second disc such that actuation of the first articulation control causes longitudinal translation of the first slider, which causes longitudinal translation of the first cable and the second cable.

5. The surgical instrument according to claim 1, wherein the second position of the end effector remains unchanged in response to actuation of the rotation mechanism.

6. The surgical instrument according to claim 1, wherein the first articulation control includes a first wheel, the second articulation control includes a second wheel, and each of the first and second wheels is selectively and independently rotatable about a rotation axis which is disposed perpendicularly to the first longitudinal axis.

7. A surgical instrument comprising:
    a handle assembly;
    an elongated shaft extending distally from the handle assembly and defining a first longitudinal axis;
    an end effector disposed in mechanical cooperation with a distal portion of the elongated shaft, the end effector defining a second longitudinal axis;
    a rotation mechanism disposed in mechanical cooperation with the handle assembly and configured to rotate the end effector about the second longitudinal axis by a rotation of at least a portion of the rotation mechanism about the first longitudinal axis relative to the handle assembly; and
    an articulation mechanism disposed in mechanical cooperation with the handle assembly and configured to move the end effector from a first position where the first longitudinal axis is aligned with the second longitudinal axis to a second position where the second longitudinal axis is displaced from the first longitudinal axis, the articulation mechanism having:
        a first articulation control disposed in mechanical cooperation with the handle assembly;
        a second articulation control disposed in mechanical cooperation with the handle assembly, the first articulation control and the second articulation control are independently actuatable with respect to each other;
        a first cable, a distal portion of the first cable disposed in mechanical cooperation with the end effector, wherein a proximal portion of the first cable is coupled to a first disc, the first disc is rotatable about the first longitudinal axis relative to the handle assembly;
a second cable, a distal portion of the second cable disposed in mechanical cooperation with the end effector,
wherein the first articulation control is actuatable in a first direction to cause the first cable to move distally with respect to the handle assembly, and wherein the second articulation control is actuatable in a second direction to cause the second cable to move distally with respect to the handle assembly.

8. The surgical instrument according to claim 7, wherein the first disc is rotatable about a second disc.

9. The surgical instrument according to claim 7, wherein the first disc is rotatable with respect to a second disc and at least a portion of the first disc is disposed at the same longitudinal position along the first longitudinal axis as at least a portion of the second disc.

10. The surgical instrument according to claim 9, wherein the second disc is rotationally fixed about the first longitudinal axis with respect to the handle assembly.

11. The surgical instrument according to claim 9, wherein the second disc defines a passageway between the handle assembly and the elongated shaft.

12. The surgical instrument according to claim 9, further including a link mechanism connecting the first articulation control to the second disc.

13. An articulation mechanism for use with a surgical instrument, the articulation mechanism comprising:
a first articulation control;
a second articulation control independently actuatable with respect to the first articulation control;
a first cable disposed in mechanical cooperation with the first articulation control;
a second cable disposed in mechanical cooperation with the first articulation control;
a third cable disposed in mechanical cooperation with the second articulation control;
a fourth cable disposed in mechanical cooperation with the second articulation control;
a disc defining a disc axis and disposed in mechanical cooperation with the first articulation control; and
a slider defining a slider axis and disposed in mechanical cooperation with the disc, the slider axis is parallel to the disc axis, and the disc is rotatable about the disc axis relative to the slider,
wherein the first articulation control is actuatable in a first direction to cause the first cable to move distally with respect to a portion of the first articulation control and to cause the second cable to move proximally with respect to the portion of the first articulation control, and wherein the second articulation control is actuatable in a second direction to cause the third cable to move distally with respect to a portion of the second articulation control and to cause the fourth cable to move proximally with respect to the portion of the second articulation control.

14. The articulation mechanism according to claim 13, wherein the first articulation control is actuatable to cause longitudinal translation of the slider.

15. The articulation mechanism according to claim 14, wherein the slider is longitudinally translatable to cause longitudinal translation of the first cable and the second cable.

16. The articulation mechanism according to claim 13, wherein the first articulation control includes a first wheel, the second articulation control includes a second wheel, and each of the first and second wheels is selectively and independently rotatable about a rotation axis.

17. The articulation mechanism according to claim 16, wherein the rotation axis is perpendicular to an axis defined by the first cable.

* * * * *